United States Patent [19]

Shapiro

[11] Patent Number: 4,758,262

[45] Date of Patent: Jul. 19, 1988

[54] HERBICIDAL PROPYLENE OXIDE DERIVATIVES

[75] Inventor: Rafael Shapiro, Wilmington, Del.

[73] Assignee: E. I. Du Pont de Nemours and Company, Wilmington, Del.

[21] Appl. No.: 806,869

[22] Filed: Dec. 13, 1985

Related U.S. Application Data

[63] Continuation-in-part of Ser. No. 699,526, Feb. 8, 1985, abandoned.

[51] Int. Cl.$^4$ .................. C07D 303/02; A01N 43/20; A01N 43/12; A01N 43/10

[52] U.S. Cl. .......................................... 71/88; 549/555; 549/557; 549/563; 549/512; 549/60; 549/469; 549/554; 71/90

[58] Field of Search .................. 71/88; 549/60, 551, 549/555, 556, 558, 559, 560, 550, 554, 557, 512; 548/252

[56] References Cited

U.S. PATENT DOCUMENTS

| | | | |
|---|---|---|---|
| 2,453,634 | 5/1944 | Marple | 549/555 |
| 2,939,872 | 6/1960 | Hudson | 549/549 |
| 3,183,074 | 5/1965 | Walworth et al. | 71/88 |
| 3,682,964 | 3/1974 | Roussel et al. | 562/405 |
| 3,930,835 | 1/1976 | Ozretich | 71/88 |
| 4,021,369 | 5/1977 | Lyons | 549/555 |
| 4,211,549 | 7/1980 | Markley et al. | 71/88 |

FOREIGN PATENT DOCUMENTS

| | | | |
|---|---|---|---|
| 38724 | 8/1985 | Australia | 549/555 |
| 4039031 | 3/1979 | Japan . | |
| 1448437 | 9/1976 | United Kingdom . | |

OTHER PUBLICATIONS

Haubenstock et al. CA(66):11271c, pp. 1117–1118, Cationic Polymerization of Epoxidesd (1967).

H. Haubenstock and W. Naegele in Makromol. Chem., 97, 248 (1986).

D. V. Gardner, et al., *J. Med. Chem.*, 22, 1373 (1979).

*Primary Examiner*—Glennon H. Hollrah
*Assistant Examiner*—D. L. Dinner

[57] ABSTRACT

This invention relates to herbicidally active propylene oxide derivatives, agriculturally suitable compositions thereof, and a method of using them as herbicides or plant growth regulants.

36 Claims, No Drawings

HERBICIDAL PROPYLENE OXIDE DERIVATIVES

RELATED U.S. APPLICATION

This is a continuation-in-part of U.S. Ser. No. 699,526 filed Feb. 8, 1985, now abandoned.

BACKGROUND OF THE INVENTION

This invention relates to herbicidally active propylene oxide compounds, agriculturally suitable compositions thereof and a method of using the compounds and the compositions as general or selective preemergent and/or post-emergent herbicides or plant growth regulants.

In the most common situation, the control of undesired vegetation is desired to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

Herbicidal compounds which exhibit sufficient selectivity, that is, which will control the growth of undesired vegetation but which will not damage useful crop plants are difficult to find. Even though there are herbicides which exhibit excellent selectivity on a number of crops while still controlling weeds at very low application rates there is a need to provide greater protection for crop plants than that provided by herbicides already disclosed. Propylene oxide derivatives of formula:

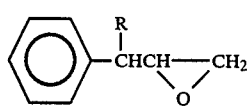
III where R is $CH_3$ or phenyl, are described by H. Haubenstock and W. Naegele in *Makromol. Chem.*, 97, 248 (1966). This article discusses the cationic polymerization of epoxides, but does not disclose any herbicidal utility for these compounds.

U.S. Pat. No. 4,211,549 discloses substituted oxirane compounds of formula

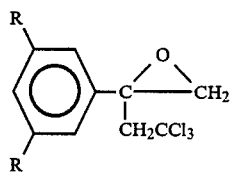

where R is Cl, Br or $CH_3$, and their use as herbicides.

Compounds of formula

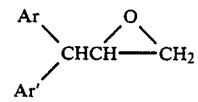

are described by D. V. Gardner, et al., *J. Med. Chem.*, 22, 1373 (1979) and in British Pat. No. 1,448,437 (published Sept. 8, 1976), as intermediates in the synthesis of certain CNS-antidepressant agents.

SUMMARY OF THE INVENTION

The present invention relates to compounds of the formula

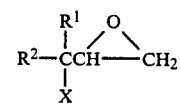
I

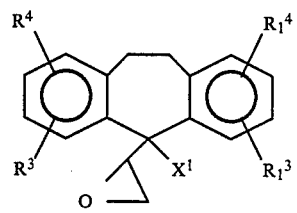
II

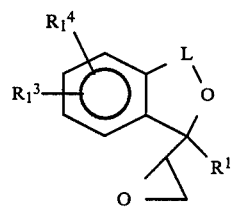
III wherein
$R^1$ is

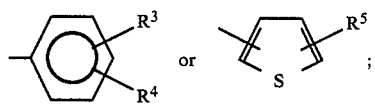

where
$R^3$, $R^4$, $R_1^3$ and $R_1^4$ are independently H, F, Cl, Br, $CF_3$, CN, $NO_2$, $OCH_2CH_2OCH_3$, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio; and
$R^5$ is H, Cl or $CH_3$;
$R^2$ is $C_2$-$C_4$ alkyl, $C_3$-$C_6$ cycloalkyl,

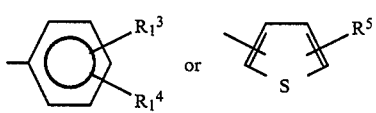

where
$R_1^3$, $R_1^4$, and $R^5$ are as previously defined;
X is F, $CH_3$, or $OR^6$;
$X^1$ is H, F, $CH_3$, or $OR^6$;
where
$R^6$ is H, $C_1$-$C_3$ alkyl, $C(O)CH_3$ or $C(O)NHCH_3$; and
L is $C(O)$, $CH_2$, $CH_2CH_2$, or $CH_2CH_2CH_2$.

The compounds of the invention are useful as general or selective preemergent and/or postemergent herbicides or plant growth regulators. The compounds of the invention are particularly useful for the control of weeds in rice.

Compounds that are preferred for reasons of increased ease of synthesis and/or greater herbicidal efficacy are:

(1) Compounds of Formulae I, II, and III where both of $R^1$ and $R^2$ are independently aryl or thienyl, $R^3$, $R^4$, $R_1^3$ and $R_1^4$ are independently H, F, Cl, Br, $CF_3$, CN, $OCH_2CH_2OCH_3$, $C_1$–$C_3$ alkyl, $C_1$–$C_3$ haloalkyl, $C_1$–$C_3$ alkoxy, $C_1$–$C_3$ haloalkoxy, $C_1$–$C_3$ alkylthio, or $C_1$–$C_3$ haloalkylthio substituted at the 3 or 4 position, and L is $CH_2$ or C(O).

(2) Compounds of Preferred 1 where $R^3$, $R^4$, $R_1^3$ and $R_1^4$ are independently H, F, Cl, $CF_3$, $C_1$–$C_3$ alkoxy, or $C_1$–$C_3$ alkyl and X and $X^1$ are OH or $OCH_3$.

Specifically preferred for reasons of greatest ease of synthesis or highest herbicidal activity or both are:
1. 2-[1-(4-chlorophenyl)-2-methylpropyl]oxirane
2. α,α-bis(4-chlorophenyl)-2-oxiranemethanol
3. α-phenyl-α-[3-(trifluoromethyl)phenyl]oxiranemethanol
4. α-(4-chlorophenyl)-α-(3-thienyl)oxiranemethanol
5. α-(4-chlorophenyl)-α-phenyloxiranemethanol
6. α,α-bis(4-fluorophenyl)-2-oxiranemethanol
7. 3-(4-fluorophenyl)-3-oxiranyl-1(3H)isobenzofuranone
8. 1-(4-fluorophenyl)-1,3-dihydro-1-oxiranyl-(R)-isobenzofuran
9. α-(4-chlorophenyl)-α-(3,5-dichlorophenyl)oxiranemethanol Another embodiment of the invention are compounds of the formula $$R^2-\underset{\underset{X}{|}}{\overset{\overset{R^1}{|}}{C}}CH\overset{O}{\overbrace{\phantom{xx}}}CH_2 \quad\quad I$$

wherein
$R^1$ is

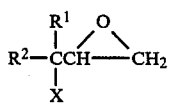

$R^2$ is $C_2$–$C_4$ alkyl, $C_3$–$C_6$ cycloalkyl, or

where
$R^3$, $R^4$, $R_1^3$ and $R_1^4$ are independently H, F, Cl, Br, $CF_3$, $OCH_2CH_2OCH_3$, $C_1$–$C_3$ alkyl, $C_1$–$C_3$ haloalkyl, $C_1$–$C_3$ alkoxy, or $C_1$–$C_3$ alkylthio;
X is $OR^6$; and
$R^6$ is H, $C_1$–$C_3$ alkyl or C(O)$CH_3$.

This invention also pertains to agriculturally suitable compositions containing mixture of the compounds of Formulae I, II, or III with Compound IVa or IVb, and their method-of-use for controlling weeds in rice.

Preferred for reasons of increased ease of synthesis, greater herbicidal activity or better selectivity or both is the combination of specifically preferred compounds 2, 3, 4, 5, 7, 8 and 9 and 2-[[(4,6-dimethoxypyrimidin-2-yl)aminocarbonyl]aminosulfonylmethyl]benzoic acid, methyl ester (IVa) or N-[(4,6-dimethoxypyrimidin-2-yl)aminocarbonyl]-1-methyl-4-ethoxycarbonyl-5-pyrazolesulfonamide (IVb) shown below:

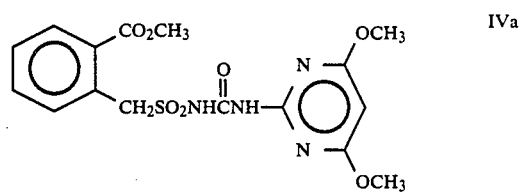

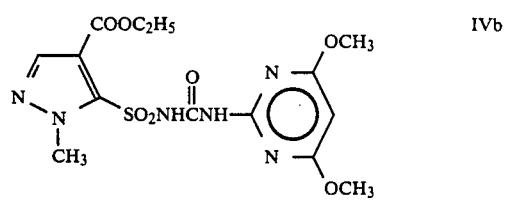

The combinations of IVa or IVb with the compounds of the present invention provide especially good results when used in growing rice.

This invention further pertains to agriculturally suitable compositions containing the compounds of Formulae I, II, and III and their method-of-use for controlling grasses in wheat. Preferred for reasons of increased ease of synthesis, greater herbicidal activity or better selectivity or both is specifically preferred compound 6.

Synthesis

Most of the compounds of Formula I may be prepared by the action of an organic peracid, such as m-chloroperbenzoic acid, on a substituted propene of Formula V, as shown in Equation 1.

Equation 1

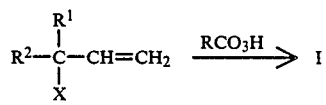

wherein R=alkyl or aryl, especially 3-ClC$_6$H$_4$, and X, $R^1$ and $R^2$ are as previously defined, provided that $R^3$, $R^4$, $R_1^3$, $R_1^4$ and $R^5$ are neither alkylthio nor haloalkylthio.

The reaction of Equation 1 is best conducted in an inert solvent such as dichloromethane at 0° to 40° C. for 1–48 hours. The product may be isolated by destroying excess peracid with aqueous sodium bisulfite, washing out the acidic by-products with aqueous sodium bicarbonate, and evaporation of solvent. Purification may be achieved by crystallization or chromatography of the residue.

The compounds of Formula V may be prepared by several methods, including those outlined in Equation 2.

Equation 2

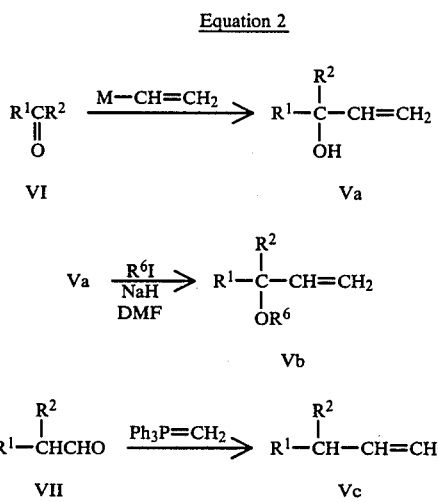

VII → Vc wherein
R¹ and R² are as defined in the Summary of the Invention, R⁶ is $C_1$–$C_3$ alkyl, and M is MgBr, MgCl or Li.

The reaction of Equation 2(a) is well known in the art, and involves the addition of one equivalent of vinylmagnesium halide (i.e., bromide or chloride) or vinyllithium to an appropriately substituted benzophenone of Formula VI. The crude product is usually of suitable purity for the next process.

Compounds of Formula Va, wherein R¹ and R² are halophenyl, are also herbicidal.

The reaction of Equation 2(b) may be conducted by contacting a compound of Formula Va in an aprotic, polar solvent such as DMF with one equivalent of a strong base, such as sodium hydride, and an excess of a lower alkyl iodide or sulfate at 25°–80° C. The product may be isolated by dilution with ice-water and extraction with a nonpolar organic solvent, such as ether or pentane, and may be purified by chromatography.

The reaction of Equation 2(c) between the disubstituted acetaldehyde of Formula VII and methylene triphenylphosphorane may be performed as described by G. Wittig and U. Schoellkopf, in *Org. Syn.*, 40, 66 (1960). The crude reaction product may be purified by chromatography or distillation.

Certain compounds of Formula I may be obtained by the action of a sulfonium or sulfoxonium methylide on the appropriate aldehyde of Formula VIII. This method, shown in Equation 3, would be useful in the preparation of sulfur-containing propylene oxide derivatives.

Equation 3

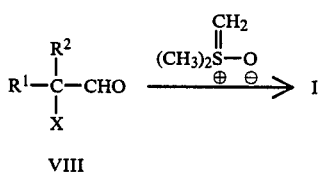

wherein R¹ and R² are as defined in the Summary of the Invention, and X is H, OH, or $C_1$–$C_3$ alkoxy.

The reaction of Equation 3 may be carried out according to the conditions described by T. Kutsuma, et al., in *Heterocycles*, 8, 397 (1977), or by the more traditional methods referenced therein.

The compounds of Formula VIII, wherein X is H, are well-known in the art. Others may be prepared according to the teachings of K. Ogura and G. Tsuchihashi, *Tetrahedron Lett.*, 2681 (1972); E. L. Eliel, et al., *J. Am. Chem. Soc.*, 100, 1615 (1978); or T. Mukaiyama et al., *Chem. Lett.*, 1253 (1978).

Other compounds of Formula I may be prepared by the action of an acylating agent on an alcohol of Formula Ia, as shown in Equation 4.

Equation 4

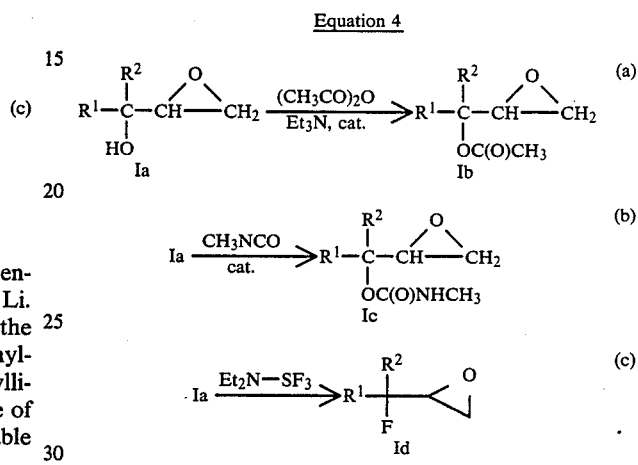

wherein R¹ and R² are as previously defined.

The reaction of Equaion 4(a) may be performed using an acetylation catalyst such as 4-dimethylaminopyridine according to W. Steglich and G. Höfle, *Angew. Chem., Int. Ed.*, 8, 981 (1969). The reaction of Equation 4(b) is performed using methyl isocyanate and di-n-butyltin dilaurate as a catalyst optionally in a solvent for 1–3 days at 25° to 60° C. The crude products Ib or Ic may be purified by crystallization or chromatography. The reaction of Equation 4(c) may be carried out by adding 0.9 to 1.1 mole-equivalents of diethylamino sulfur trifluoride to a solution of Ia in dichloromethane at −30° to 20° C., washing the reaction mixture with aqueous NaHCO₃, and concentration. If necessary, the crude product, Id, may be purified by chromatography.

Another method by which compounds of Formulat Ia may be prepared is the reaction of a lithioarene of Formula X with an α,β-epoxyketone of Formula XI, as shown in Equation 5. The ketones may be prepared as described for 4'-methoxy-2,3-epoxypropiophenone (A. P. Beracierta and D. A. Whiting, *J. Chem. Soc. Perkin 1*, 1978, 1257.)

Equation 5

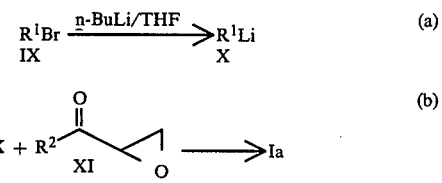

The reaction of Equation 5(a) is conducted by cooling a solution of an arylbromide in an ethereal solvent such as tetrahydrofuran to −78° to −110° C. and adding 0.9 to 1.1 equivalents of a solution of n-butyllithium in an inert solvent such as hexane. In the same flask, the reaction of Equation 5(b) is performed by adding a solution of the appropriate epoxy-ketone XI in an ethereal solvent such as tetrahydrofuran and allowing the reaction mixture to warm to 0° to 25° C. for 0.1 to 1 hour. The product may be isolated by quenching with a weak acid such as aqueous ammonium chloride, extraction, concentration, and trituration or chromatography.

The compounds of Formula II may be prepared by direct analogy with the methods described for those of Formula I in Equations 1, 2, 3 and 4, starting with the appropriately substituted dibenzocycloheptadienones.

Compounds of Formula III may be prepared by the methods outlined in Equations 6 and 7.

Equation 6

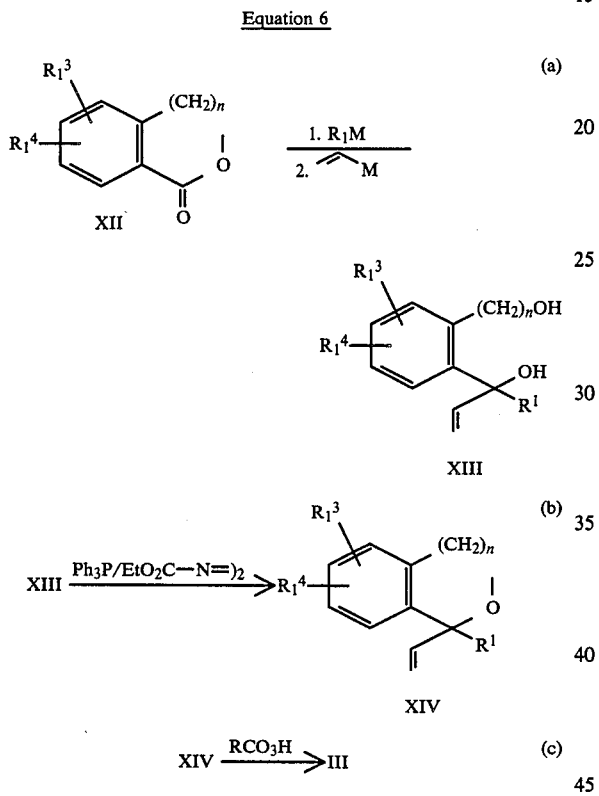

wherein

R, $R^1$, $R_1^3$, and $R_1^4$ are as defined in Equation 1, n is 1 or 2, and M is MgBr, MgCl or Li.

In the reaction of Equation 6a, an appropriately substituted phthalide (n=1) or dihydroisochromanone (n=2) is contacted in an ethereal solvent with one equivalent of an aryl Grignard or lithium reagent at low temperatures (−78° to 0° C.). The reaction product may be isolated by standard procedures, or the reaction mixture may be directly contacted with one equivalent of a vinyl lithium or a vinyl Grignard solution. The product may be isolated after reaction at 0°-50° C. by the addition of aqueous NH4Cl and extraction into an organic solvent. Purification may be achieved by crystallization or chromatography to afford the compounds of Formula XIII. Cyclization to the compounds of Formula XIV may be performed by contacting a mixture of one equivalent of XIII with 1.1–1.5 equivalents of triphenylphosphine in an inert solvent such as dichloromethane or THF, and adding 1.1–1.5 equivalents of diethylazodicarboxylate. After 1–20 hours, the reaction mixture may be filtered through silica gel to provide the cyclic ethers of Formula XIV as a mixture of diastereomers, which may then be oxidized as described for Equation 1. The resulting epoxide mixture may then be separated by silica gel chromatography, or may be utilized as such.

Other compounds of Formula III may be prepared from the corresponding 2-aroylbenzoic acids as outlined in Equation 7.

Equation 7

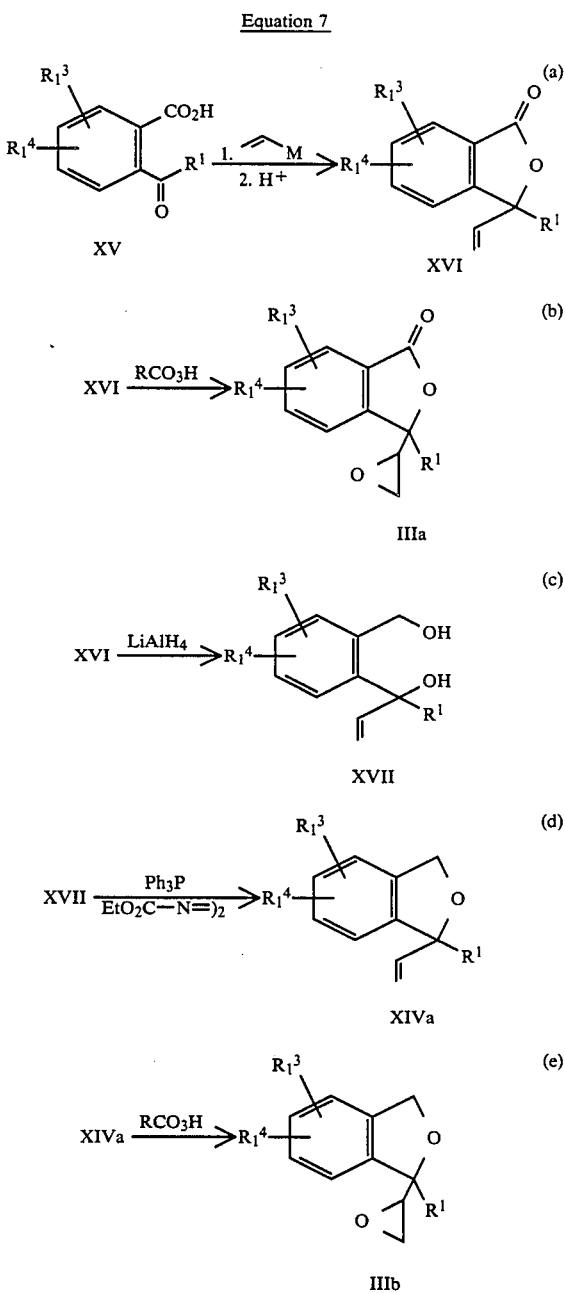

wherein

R, $R^1$, $R_1^3$ and $R_1^4$ are as defined in Equation 1, and M=MgBr, MgCl or Li.

The reaction of Equation 7a may be carried out by adding 2.0 to 2.5 equivalents of the vinyl Grignard or vinyl lithium solution to the appropriate ketone of Formula XV in an ethereal solvent such as THF at −20° to 35°. After the reaction mixture is acidified with aqueous mineral acid, the product of Formula XVI may be isolated by extraction into an organic solvent and concentration. The reaction of Equation 7b may be performed as described for that of Equation 1. Alternatively, the phthalide of Formula XVI may be reduced to the diol of Formula XVII by a hydride donor such as lithium aluminum hydride. This reaction may be conducted by adding 0.5 to 1 mole-equivalents of the reagent to XVI in a solvent such as diethyl ether at −20° to 20°, stirring for 0.1 to 1 hour, adding aqueous NaOH to precipitate inorganic salts, and filtration. The compound of Formula XVII may be isolated by evaporation of the solvent. The reactions of Equations 7d and 7e are then performed as described for those of Equations 6b and 6c, respectively. 2-[[(4,6-Dimethoxypyrimidin-2-yl)aminocarbonyl]aminosulfonylmethyl]benzoic acid, methyl ester is a known herbicide and may be synthesized according to the methods taught in U.S. Pat. No. 4,420,325 (issued Dec. 13, 1983), which is herein incorporated by reference.

N-[(4,6-Dimethoxypyrimidin-2-yl)aminocarbonyl]-1-methyl-4-ethoxycarbonyl-5-pyrazolesulfonamide is a known herbicide and may be synthesized according to the methods taught in EP-A No. 95,925 (published Dec. 7, 1983), which is herein incorporated by reference.

One skilled in the art will recognize that many of the compounds of Formulae I, II, and III can contain up to two asymmetric carbon atoms (e.g., when $R^1 \neq R^2$). The resulting diastereoisomers both possess herbicidal utility and their separation is optional.

The following examples further illustrate the preparation of compounds of Formulae I, II and III. Unless otherwise noted, temperatures are reported in degrees Celsius.

EXAMPLE 1

3-p-Chlorophenyl-4-methyl-1-pentene

To a solution of 10.0 g of 4-chloro-α-[2-methylethyl]-benzeneacetonitrile in 100 mL of tetrahydrofuran was added 55 mL of 1M diisobutylaluminum hydride in toluene. The reaction mixture was stirred for 2 hours at 25°, cooled to 0°, and treated with 1 mL of methanol, then 40 mL of 10% aqueous HCl. The mixture was extracted with 100 mL of ether, washed with brine, dried (MgSO$_4$), and concentrated to dryness. The crude product (a 2:1 mixture of aldehyde and starting nitrile) was used in the next step. The mixture was dissolved in ether and added to methylene triphenylphosphorane (prepared by adding 28 mL of 1.6M n-butyllithium in hexane to 16 g of methyl triphenylphosphonium bromide in 150 mL of ether at 0°). The reaction mixture was stirred at 25° overnight, quenched with 2 mL of absolute EtOH, and filtered. The filtrate was washed with water, brine, dried (MgSO$_4$), and concentrated. The residue was "chromatographed" on silica gel; elution with hexane provided 4.6 g of the title compound.

NMR (CDCl$_3$): δ0.7 (d, 3H), 0.95 (d, 3H), 1.9 (m, 1H), 2.9 (t, 1H), 4.9–6.2 (m, 3H), 7.3 (AB quartet, 4H).

EXAMPLE 2

2-[1-(4-Chlorophenyl)-2-methylpropyl]oxirane

A mixture of 4 g of the product of Example 1 and 4.5 g of m-chloroperbenzoic acid in 50 mL of chloroform was stirred overnight at room temperature and filtered. The filtrate was washed with aqueous NaHSO$_3$, aqueous NaHCO$_3$, brine, dried (Na$_2$SO$_4$), and concentrated. The residue was a mixture of diastereomeric epoxides.

NMR (CDCl$_3$): δ0.8 (d of d, 3H) 1.1 (two d of d, 3H), 2.0 (m, 1H), 2.4–3.0 (m), 3.2 (m, 1H), 7.3 (m, 4H).

EXAMPLE 3

α,α-bis(4-Chlorophenyl)oxiranemethanol

To a solution of 6 g of 4,4'-dichlorobenzophenone in 200 mL of ether was added 30 mL of 1.4M vinylmagnesium bromide/THF at 0°. After being stirred at 25° for 20 minutes, the mixture was poured onto aqueous NH$_4$Cl, partitioned, washed with brine, dried (MgSO$_4$), filtered, and concentrated. The crude adduct was allowed to stand in 50 mL of methylene chloride with 5.8 g of m-chloroperbenzoic acid for 3 days at 25°. The mixture was diluted with CH$_2$Cl$_2$, washed with aqueous NaHSO$_3$, aqueous NaHCO$_3$, brine, dried (Na$_2$SO$_4$), concentrated, and chromatographed (150 mL SiO$_2$/30% CH$_2$Cl$_2$ in hexane) to provide 2.9 g of the title compound (after washing the concentrated fractions with pentane), m.p. 87°–88°.

NMR (CDCl$_3$): δ2.7 (s, 1H), 2.8 (m, 1H), 2.9 (m, 1H), 3.7 (m, 1H), 7.4 (m, 8H).

EXAMPLE 4

(α,α-bis(4-Fluorophenyl)-2-oxiranyl)methyl acetate

To a solution of 0.7 g of α,α-bis(4-fluorophenyl)oxiranemethanol (prepared as described above for the chloro analog) in 1 mL of triethylamine and 1 mL of acetic anhydride was added 50 mg of 4-dimethylaminopyridine. The mixture was allowed to stand at 25° for 3 days, partitioned between ether and water, washed with aqueous NaHCO$_3$, aqueous oxalic acid, aqueous NaHCO$_3$, brine, dried (MgSO$_4$), and concentrated. The residue was chromatographed and triturated with pentane to provide 0.7 g of the title compound, m.p. 88°–90°.

NMR (CDCl$_3$): δ2.1 (d of d, 1H), 2.2 (2, 3H), 2.8 (t, 1H), 4.5 (d of d, 1H), 7.0 (d of t, J=2, 9 Hz), 7.35 (d of d, J=6, 9 Hz).

EXAMPLE 5

α-(4-Chlorophenyl)-α-(2-fluorophenyl)oxiranemethanol

To a solution of 0.9 g of 2-bromofluorobenzene in 10 mL of THF and 20 mL of diethyl ether was added 3.2 mL of a 1.6M solution of n-butyllithium in hexanes at −78°. After the addition was complete, a solution of 0.9 g of 4'-chloro-2,3-epoxypropiophenone (J.T. Lumb, *Tetrahedron Lett.*, 1970, 579) in 5 mL of ether was added, and the reaction mixture was allowed to warm to room temperature. After being quenched with 10 mL of saturated NH$_4$Cl (aqueous), the mixture was separated, the organic phase was washed with brine, dried (MgSO$_4$), filtered, concentrated, and triturated with hexanes to afford 1.0 g of the title compound, m.p. 120°–122°.

NMR (CDCl$_3$): δ2.81 (s, 1H), 2.88 (t, 1H), 3.03 (d of d, 1H), 3.87 (m, 1H), 7.0 (d of d, 1H), 7.32 (m, 6H), 7.78 (d of t, 1H).

Using the procedures described in Equations 1–7 and Examples 1–5 above, one skilled in the art can prepare the compounds shown in Tables 1–5.

Table of Structures

General Structure 1
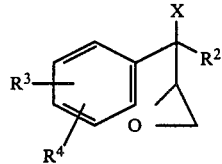

General Structure 2
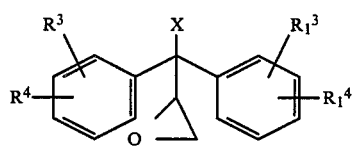

General Structure 3
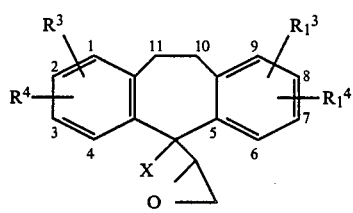

-continued
Table of Structures

General Structure 4
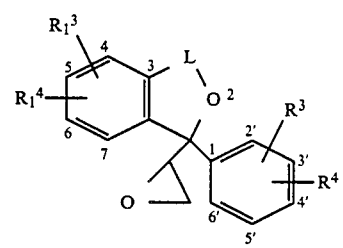

General Structure 5
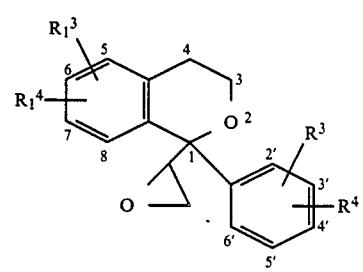

TABLE 1
General Structure I

| Cmpd. No. | $R^2$ | $R^3$ | $R^4$ | X | m.p.(°C.) |
|---|---|---|---|---|---|
| 1 | $CH_3$ | 4-Cl | H | OH | 59-61 (isomer A) |
| 2 | $CH_3$ | 4-Cl | H | OH | oil (1:1 mixture of isomers) |
| 3 | $CH_3$ | 4-F | H | OH | |
| 4 | $CH_3$ | 3-F | 4-F | OH | |
| 5 | $CH_3$ | 4-$CF_3$ | 4-F | OH | |
| 6 | $CH_3$ | 3-CN | 4-F | H | |
| 7 | $CH_3$ | 3-Cl | 4-F | OH | |
| 8 | $C_2H_5$ | 3-Cl | 4-F | H | |
| 9 | $C_2H_5$ | 4-F | 4-F | OH | |
| 10 | $C_2H_5$ | 4-$CH_3$ | 4-F | OH | |
| 11 | $C_2H_5$ | 4-CN | 4-F | OH | |
| 12 | $C_2H_5$ | 3-F | 4-$OCH_2CH_3$ | OH | |
| 13 | $C_2H_5$ | 3-$CF_3$ | H | OH | |
| 14 | n-$C_3H_7$ | 3-Cl | H | OH | |
| 15 | n-$C_3H_7$ | 3-F | H | H | |
| 16 | n-$C_3H_7$ | 4-F | H | $OCH_3$ | |
| 17 | n-$C_3H_7$ | 4-Br | H | OH | |
| 18 | n-$C_3H_7$ | 4-$CF_3$ | H | $OCOCH_3$ | |
| 19 | n-$C_3H_7$ | 4-$OCF_3$ | H | OH | |
| 20 | i-$C_3H_7$ | 4-Cl | H | H | oil |
| 21 | i-$C_3H_7$ | 4-Cl | H | OH | 75-76.5 (isomer A) |
| 22 | i-$C_3H_7$ | 4-Cl | H | OH | 73-74 (isomer B) |
| 23 | i-$C_3H_7$ | 4-Cl | H | $OCH_3$ | |
| 24 | i-$C_3H_7$ | 4-$OCH_3$ | H | H | |
| 25 | i-$C_3H_7$ | 3-Cl | H | H | |
| 26 | i-$C_3H_7$ | 2-Cl | H | H | oil |
| 27 | i-$C_3H_7$ | 3-Cl | H | OH | |
| 28 | i-$C_3H_7$ | 3-$CH_3$ | 4-F | OH | |
| 29 | i-$C_3H_7$ | 3-F | H | OH | |
| 30 | i-$C_3H_7$ | 4-F | H | OH | |
| 31 | i-$C_3H_7$ | H | H | OH | |
| 32 | i-$C_3H_7$ | H | H | H | oil |
| 33 | n-$C_4H_9$ | 4-Cl | H | OH | |
| 34 | n-$C_4H_9$ | 4-F | H | OH | 53-54 |
| 35 | n-$C_4H_9$ | 3-F | H | H | |
| 36 | n-$C_4H_9$ | 3-Cl | H | OH | |
| 37 | i-$C_4H_9$ | 4-$OCF_3$ | H | OH | |
| 38 | i-$C_4H_9$ | 3-$CF_3$ | H | OH | |
| 39 | i-$C_4H_9$ | 3-$CH_2CH_3$ | 4-F | OH | |
| 40 | i-$C_4H_9$ | 4-F | H | OH | |
| 41 | i-$C_4H_9$ | 3-Cl | H | OH | |
| 42 | i-$C_4H_9$ | 4-CN | H | OH | |
| 43 | s-$C_4H_9$ | 2-F | H | OH | |
| 44 | s-$C_4H_9$ | 3-F | H | $OCH_3$ | |
| 45 | s-$C_4H_9$ | 4-Br | H | OH | |
| 46 | s-$C_4H_9$ | H | H | OH | |

TABLE 1-continued

General Structure I

| Cmpd. No. | R² | R³ | R⁴ | X | m.p.(°C.) |
|---|---|---|---|---|---|
| 47 | s-C₄H₉ | 3-OCH₃ | H | OH | |
| 48 | t-C₄H₉ | 4-SCH₃ | H | OH | |
| 49 | t-C₄H₉ | 3-F | 4-F | OH | |
| 50 | t-C₄H₉ | 4-OCH₂CH₂OCH₃ | H | OH | |
| 51 | t-C₄H₉ | 4-Cl | H | OH | 110–118 |
| 52 | cyclopropyl | 3-Cl | H | OH | |
| 53 | cyclopropyl | 3-F | H | OH | |
| 54 | cyclopropyl | 3-CN | H | OH | |
| 55 | cyclobutyl | 4-Cl | 3-Cl | OH | |
| 56 | cyclobutyl | 4-F | H | OH | |
| 57 | cyclobutyl | 3-Cl | H | OH | |
| 58 | cyclopentyl | 3-F | H | OH | |
| 59 | cyclopentyl | 4-F | H | H | |
| 60 | cyclopentyl | 4-SCHF₂ | H | OH | |
| 61 | cyclopentyl | 4-CF₃ | H | OH | |
| 62 | cyclopentyl | 3-Cl | 5-Cl | OH | |
| 63 | cyclohexyl | 3-CF₃ | H | OH | |
| 64 | cyclohexyl | 3-F | H | OH | |
| 65 | cyclohexyl | 4-Cl | H | OH | |
| 66 | cyclohexyl | 4-OCF₃ | H | OH | |

TABLE 2

General Structure 1

| Cmpd. No. | R² | R³ | R⁴ | X | R⁵ | m.p. (°C.) |
|---|---|---|---|---|---|---|
| 67 | 2-thienyl | H | H | OH | H | |
| 68 | 2-thienyl | 4-F | H | OH | H | |
| 69 | 2-thienyl | 4-Cl | H | OH | H | 105–105.5 |
| 70 | 2-thienyl | 3-F | H | OH | H | |
| 71 | 2-thienyl | 3-F | 4-F | H | H | |
| 72 | 2-thienyl | 3-CH₃ | H | OH | H | |
| 73 | 2-thienyl | 3-Cl | H | OH | H | |
| 74 | 3-thienyl | H | H | OH | H | |
| 75 | 3-thienyl | 4-CF₃ | H | OH | H | |
| 76 | 3-thienyl | 3-F | H | OH | H | |
| 77 | 3-thienyl | 4-F | H | OCH₃ | H | |
| 78 | 3-thienyl | 4-Cl | H | OH | H | 106–107 |
| 79 | 3-thienyl | 3-Cl | H | OH | H | |
| 80 | 3-thienyl | 3-CN | H | OH | H | |
| 81 | 3-thienyl | 3-CH₂CH₃ | H | OH | H | |
| 82 | 2-thienyl | 3-F | H | OH | 5-Cl | 81–81.5 |
| 83 | 2-thienyl | 4-F | H | OH | 5-Cl | |
| 84 | 2-thienyl | 3-Cl | 5-Cl | OH | 5-Cl | |
| 85 | 2-thienyl | H | H | OH | 5-CH₃ | |
| 86 | 2-thienyl | 4-OCH₃ | H | OH | 5-CH₃ | |
| 87 | 2-thienyl | 4-SCH₃ | H | OH | 5-CH₃ | |
| 88 | 2-thienyl | 3-CN | H | OH | 3-CH₃ | |
| 89 | 2-thienyl | 3-CF₃ | H | OH | 5-CH₃ | |
| 90 | 2-thienyl | 4-F | H | OH | 5-CH₃ | |
| 91 | 3-thienyl | 4-F | H | OH | 5-CH₃ | |
| 92 | 3-thienyl | 4-F | H | OCOCH₃ | 4-Cl | |
| 93 | 3-thienyl | 3-F | 3-CF₃ | OH | 4-Cl | |
| 94 | 3-thienyl | 3-Cl | H | OH | 4-Cl | |
| 95 | 3-thienyl | 3-Cl | H | OCH₃ | 4-Cl | |
| 96 | 3-thienyl | 3-Cl | H | OH | 2-Cl | |
| 97 | 3-thienyl | 3-Cl | H | OCOCH₃ | 2-Cl | |
| 98 | 3-thienyl | 3-Cl | H | OCH₃ | 2-Cl | |
| 99 | 3-thienyl | 3-Cl | H | OH | 4-CH₃ | |

TABLE 3

General Structure 2

| Cmpd. No. | R³ | R⁴ | R₁³ | R₁⁴ | X | m.p.(°C.) |
|---|---|---|---|---|---|---|
| 100 | 4-F | H | 2'-F | H | OH | 97–102 |
| 101 | 4-F | H | 4'-F | H | CH₃ | oil |
| 102 | 4-F | H | 4'-F | H | OCH₃ | oil |
| 103 | 4-F | H | 4'-CF₃ | H | OH | 101–102.5 |
| 104 | 4-F | H | 4'-OCH₃ | H | OH | 97–98.5 |
| 105 | 4-F | H | 4'-SCH₃ | H | OH | 108–110 |
| 106 | 4-F | H | 3'-CN | H | OH | 86–90 |
| 107 | 4-F | H | 4'-Br | H | OH | 89–91 |
| 108 | 4-F | H | 3'-Cl | 5'-Cl | OH | 127–128.5 |
| 109 | 4-F | H | 3'-CF₃ | H | OH | 98–98.5 |
| 110 | 4-F | H | 2'-F | 5'-F | OH | 136–140 |
| 111 | 4-F | H | 4'-CH₃ | H | OH | 84–85 |
| 112 | 4-F | H | 3'-CH₃ | H | OH | 81–82.5 |
| 113 | 4-F | H | 2'-CH₃ | H | OH | 131–132 |
| 114 | 4-F | H | 4'-F | H | H | oil |
| 115 | 4-F | H | 4'-Cl | H | OH | 104–106 |
| 116 | 4-F | H | 3'-CF₃ | 5'-CF₃ | OH | 83–84 |
| 117 | 4-F | H | 3'-F | 4'-F | OH | 91–92 |
| 118 | 4-F | H | 3'-Cl | H | OH | 88 |
| 119 | 4-F | H | 4'-F | H | F | oil |
| 120 | 4-F | H | 4'-F | H | OH | 145–147 |
| 121 | 4-F | H | 4'-F | H | OCOCH₃ | 88–90 |
| 122 | 4-F | H | 3'-Cl | 4'-Cl | OH | |
| 123 | 4-F | H | H | H | OH | |
| 124 | 4-F | H | H | H | OCH₃ | |

TABLE 3-continued

General Structure 2

| Cmpd. No. | $R^3$ | $R^4$ | $R_1^3$ | $R_1^4$ | X | m.p.(°C.) |
|---|---|---|---|---|---|---|
| 125 | 4-F | 3-CH$_3$ | 3'-Cl | 4'-F | OH | |
| 126 | 4-F | H | 3'-F | H | OCH$_3$ | |
| 127 | 4-F | H | 3'-Cl | H | OCOCH$_3$ | |
| 128 | 4-F | H | 3'-CH$_3$ | H | OCH$_3$ | |
| 129 | 4-F | H | 3'-CN | H | OCOCH$_3$ | |
| 130 | 4-F | H | 2'-F | 3'-F | OCOCH$_3$ | |
| 131 | 4-F | H | 3'-F | 4'-F | OCONHCH$_3$ | |
| 132 | 4-F | H | 4'-Cl | H | OCH$_3$ | |
| 133 | 3-F | H | 3'-F | H | OH | 117–119 |
| 134 | 3-F | H | 4'-F | H | OH | 86–87 |
| 135 | 3-F | H | 3'-CN | H | OH | 119–121.5 |
| 136 | 3-F | H | 3'-F | 4'-F | OH | 86–89 |
| 137 | 3-F | 4-F | 3'-F | 4'-F | OH | 96–97 |
| 138 | 3-F | H | 3'-F$_3$C | H | OH | oil |
| 139 | 3-F | H | 2'-F | H | OH | |
| 140 | 3-F | H | 2'-Cl | H | OH | |
| 141 | 3-F | H | 3'-F | H | OCH$_3$ | |
| 142 | 3-F | H | 4'-CN | H | OH | |
| 143 | 3-F | H | 4'-Cl | H | OH | |
| 144 | 3-F | H | 4'-Cl | H | OCH$_3$ | |
| 145 | 3-F | H | 4'-Cl | H | CH$_3$ | |
| 146 | 3-F | H | 3'-Cl | 5'-Cl | OH | |
| 147 | 3-F | H | 3'-Cl | 4'-Cl | OH | |
| 148 | 3-F | H | 3'-Cl | 4'-Cl | OCH$_3$ | |
| 149 | 3-F | 4-Cl | 3'-CH$_3$ | 4'-Cl | OH | |
| 150 | 3-F | H | 3'-CH$_3$ | 4'-CH$_3$ | OH | |
| 151 | 3-F | H | 3'-CH$_3$ | H | OH | |
| 152 | 3-F | H | 4'-CH$_3$ | H | OH | |
| 153 | 3-F | H | 4'-CH$_3$ | H | OCH$_3$ | |
| 154 | 3-F | H | H | H | OH | |
| 155 | 3-Cl | H | H | H | OH | |
| 156 | 3-Cl | H | H | H | H | |
| 157 | 3-Cl | H | 3'-Cl | H | OH | |
| 158 | 3-Cl | H | 3'-Cl | 5'-Cl | OH | |
| 159 | 3-Cl | H | 3'-Cl | 4'-Cl | OH | |
| 160 | 3-Cl | H | 4-CH$_3$ | H | OH | |
| 161 | 3-Cl | H | 4-CF$_3$ | H | OH | |
| 162 | 3-Cl | H | 3-CF$_3$ | H | OCH$_3$ | |
| 163 | 3-Cl | H | 4-Br | H | OH | |
| 164 | 3-Cl | H | 4-OCH$_3$ | H | OH | |
| 165 | 4-Cl | H | 4-SCH$_3$ | H | OH | 89–90 |
| 166 | 4-Cl | H | 3-CN | H | OH | 79–82 |
| 167 | 4-Cl | H | 4-Cl | 3-CF$_3$ | OH | 102–104 |
| 168 | 4-Cl | H | 3-Cl | 5-Cl | OH | 130–131 |
| 169 | 4-Cl | H | 4-Cl | H | H | oil |
| 170 | 4-Cl | H | 4-Cl | H | F | oil |
| 171 | 4-Cl | H | 4-Cl | H | OH | 87–88 |
| 172 | 4-Cl | H | 2-F | 5-F | OH | 133–137 |
| 173 | 4-Cl | H | 4-Cl | H | OCH$_3$ | oil |
| 174 | 4-Cl | H | 4-Cl | H | OCONHCH$_3$ | oil |
| 175 | 4-Cl | H | 4-Cl | H | OCOCH$_3$ | oil |
| 176 | 4-Cl | H | 4-OCH$_3$ | H | OH | 88–91 |
| 177 | 4-Cl | H | 4-F | H | OH | 90–95 |
| 178 | 4-Cl | H | 4-CH$_3$ | H | OH | |
| 179 | 4-Cl | H | 3-CH$_3$ | H | OH | |
| 180 | 4-Cl | H | 2-F | H | OCH$_3$ | 120–122 |
| 181 | 4-Cl | H | 4-OCF$_3$ | H | OH | |
| 182 | 4-Cl | H | 3-CF$_3$ | H | OH | |
| 183 | 4-Cl | H | 4-CF$_3$ | H | OH | |
| 184 | 4-Cl | H | H | H | OH | |
| 185 | 4-Cl | H | H | H | OCH$_3$ | |
| 186 | 4-Cl | H | H | H | OCOCH$_3$ | |
| 187 | 4-Cl | H | 3-CF$_3$ | H | OH | |
| 188 | 4-Cl | H | 4-Br | H | OH | |
| 189 | 4-Cl | H | 3-Cl | 4-Cl | OH | |
| 190 | 4-Cl | H | 3-Cl | H | OH | |
| 191 | 4-Cl | H | 3-Cl | H | OCH$_3$ | |
| 192 | 4-Cl | H | 2-Cl | H | OH | |
| 193 | 4-Cl | H | 3-Cl | 5-Cl | OH | 130–131 |
| 194 | 4-Cl | H | 3-Cl | 4-CF$_3$ | OH | |
| 195 | 4-Cl | 3-CF$_3$ | 3-Cl | H | OH | |
| 196 | 4-Cl | H | i-C$_3$H$_7$ | H | OH | |
| 197 | 4-Cl | H | 4-CN | H | OH | 126–129 |
| 198 | 2-Cl | H | 2-Cl | H | OH | 115–116 |
| 199 | 3-Cl | H | 3-CN | H | OH | |
| 200 | 3-Cl | H | 4-CN | H | OCH$_3$ | |
| 201 | 3-Cl | H | 4-CHF$_2$ | H | OH | |
| 202 | 3-Cl | H | 2-Cl | 5-Cl | CH$_3$ | |
| 203 | 3-Cl | H | H | H | F | |

TABLE 3-continued

General Structure 2

| Cmpd. No. | R³ | R⁴ | R₁³ | R₁⁴ | X | m.p.(°C.) |
|---|---|---|---|---|---|---|
| 204 | 3-Cl | H | H | H | OH | |
| 205 | 3-Cl | 4-CN | 4-Cl | H | OH | |
| 206 | 3-Cl | H | 4-Cl | 4-Cl | OH | |
| 207 | 3-Cl | H | 3-Cl | 5-Cl | OH | |
| 208 | 2-CF₃ | H | H | H | OH | 72–74 |
| 209 | 3-CF₃ | H | 4-CF₃ | H | OH | |
| 210 | 3-CF₃ | H | 3-CF₃ | H | OH | 74.5–77 |
| 211 | 4-CF₃ | H | 4-CF₃ | H | OH | 109–110 |
| 212 | 4-CF₃ | H | H | H | OH | 85–86 |
| 213 | 3-CF₃ | H | H | H | OH | 68–70 |
| 214 | H | H | H | H | OH | 117–121 |
| 215 | H | H | H | H | OCH₃ | |
| 216 | H | H | H | H | OCOCH₃ | |
| 217 | H | H | H | H | F | |
| 218 | H | H | H | H | CH₃ | |
| 219 | 3-CH₃ | H | H | H | OH | |
| 220 | 3-CH₃ | H | 3-CH₃ | H | OH | |
| 221 | 3-CH₃ | H | 3-OCH₃ | H | OH | |
| 222 | 3-CH₃ | H | 4-SCH₃ | H | OH | |
| 223 | 3-CH₃ | 4-CH₃ | 4-Cl | H | OCH₃ | |
| 224 | 3-CH₃ | H | 4-Br | H | OH | |
| 225 | 4-CH₃ | H | 4-CH₃ | H | OH | oil |
| 226 | 4-CH₃ | H | 3-CN | H | OH | |
| 227 | 4-CH₃ | H | 4-CN | H | OH | |
| 228 | 4-CH₃ | H | H | H | OH | |
| 229 | 4-CH₃ | H | OCH₂CH₂OCH₃ | H | H | |
| 230 | 4-CH₃ | H | 3-Cl | 4-Cl | H | |
| 231 | 4-CH₃ | H | 4-NO₂ | H | OH | |
| 232 | 3-OCH₃ | H | 3-CH₃ | 4-F | OH | |
| 233 | 3-OCH₃ | H | 3-Cl | 5-Cl | OH | |
| 234 | 3-OCH₃ | H | H | H | OH | |
| 235 | 3-OCH₃ | 4-F | 3-Cl | 4-Cl | OH | |
| 236 | 3-OCH₃ | H | 3-OCF₃ | H | H | |
| 237 | 3-OCH₃ | H | 4-SCF₂H | H | OH | |
| 238 | 3-OCH₃ | H | 4-CH₂CH₃ | H | OCOCH₃ | |
| 239 | 4-OCH₃ | H | 3-OCH₃ | H | OH | |
| 240 | 4-OCH₃ | H | 3-CN | H | OH | |
| 241 | 4-OCH₃ | H | 3-F | 4-CN | OH | |
| 242 | 4-OCH₃ | H | 2-CH₃ | H | OH | |
| 243 | 4-OCH₃ | H | 4-Br | H | OH | |
| 244 | 4-OCH₃ | H | H | H | H | |
| 245 | 4-OCH₃ | H | 3-CF₃ | H | OH | |

TABLE 4

General Structure 3

| Cmpd. No. | R³ | R⁴ | R₁³ | R₁⁴ | X | m.p. (°C.) |
|---|---|---|---|---|---|---|
| 246 | H | H | H | H | OH | 132–133 |
| 247 | H | H | H | H | OCH₃ | |
| 248 | H | H | H | H | OCOCH₃ | |
| 249 | H | H | H | H | F | |
| 250 | 1-F | H | H | H | OH | 144–145 |
| 251 | 2-F | H | H | H | OH | 118–120 |
| 252 | 3-F | H | H | H | OH | 114–124 |
| 253 | 2-F | H | 8-F | H | OH | 146–147 |
| 254 | H | H | H | H | H | |
| 255 | H | H | H | H | CH₃ | |
| 256 | 2-F | H | 8-Cl | H | OH | |
| 257 | 3-F | H | H | H | OH | |
| 258 | 4-F | H | H | H | OH | |
| 259 | 2-Cl | H | H | H | OH | |
| 260 | 3-Cl | H | 8-F | H | OH | |
| 261 | 2-CH₃ | H | H | H | OH | |
| 262 | 3-CH₃ | H | 7-CH₃ | 8-CH₃ | OH | |
| 263 | 2-CN | H | H | H | OCH₃ | |
| 264 | 3-CN | H | H | H | OH | |
| 265 | 2-CF₃ | H | H | H | OH | |
| 266 | 3-CF₃ | H | H | H | OH | |
| 267 | 2-F | 3-Cl | H | H | OH | |
| 268 | 3-F | H | H | H | OH | |
| 269 | 2-Cl | H | H | H | OH | |
| 270 | 3-Cl | H | H | H | OH | |
| 271 | 2-CF₃ | 3-F | H | H | OH | |
| 272 | 3-CF₃ | H | 7-CF₃ | H | OH | |
| 273 | 1-F | H | 9-F | H | OH | |

TABLE 5

General Structure 4

| Cmpd. No. | R₁³ | R₁⁴ | R³ | R⁴ | L | m.p. (°C.) |
|---|---|---|---|---|---|---|
| 274 | H | H | H | H | CH₂ | |
| 275 | H | H | 4'-F | H | C=O | oil |
| 276 | H | H | 4'-F | H | CH₂ | oil (diast. A) |
| 277 | H | H | 4'-F | H | CH₂ | oil (diast. B) |
| 278 | H | H | 4'-Cl | H | CH₂ | oil |
| 279 | H | H | 4'-Cl | H | C=O | oil |
| 280 | H | H | 3'-F | H | CH₂ | oil |
| 281 | 5-F | H | 4'-F | H | CH₂ | oil |
| 282 | H | H | 3'-CH₃ | H | CH₂ | |
| 283 | H | H | 3'-CN | H | CH₂ | |
| 284 | H | H | 4'-CF₃ | H | CH₂ | |
| 285 | H | H | 4'-CN | H | CH₂ | |
| 286 | H | H | 4'-OCH₃ | H | CH₂ | |
| 287 | H | H | 3'-F | 4'-F | CH₂ | |
| 288 | 4-F | H | 4'-F | H | CH₂ | |
| 289 | 5-Cl | H | 3'-F | H | CH₂ | |
| 290 | 6-Cl | H | 3'-Cl | H | CH₂ | |
| 291 | 6-F | 4-Cl | 3'-CN | H | CH₂ | |

TABLE 5-continued

General Structure 4

| Cmpd. No. | $R_1^3$ | $R_1^4$ | $R^3$ | $R^4$ | L | m.p. (°C.) |
|---|---|---|---|---|---|---|
| 292 | 5-CH$_3$ | H | 4'-CH$_3$ | 3'-F | CH$_2$ | |
| 293 | 6-CH$_3$ | H | 3'-CH$_3$ | H | CH$_2$ | |
| 294 | 4-Cl | H | 3'-F | H | CH$_2$ | |
| 295 | H | H | H | H | C=O | |
| 296 | H | H | 4'-Cl | H | C=O | |
| 297 | H | H | 3'-Cl | 4'-Cl | C=O | |
| 298 | H | H | 4'-CF$_3$ | H | C=O | |
| 299 | H | H | 4'-CN | H | C=O | |
| 300 | 5-F | H | 3'-CH$_3$ | H | C=O | |
| 301 | 6-F | H | 3'-Cl | H | C=O | |
| 302 | H | H | 4'-F | 3'-F | C=O | |

TABLE 6

General Structure 5

| Cmpd. No. | $R_1^3$ | $R_1^4$ | $R^3$ | $R^4$ | m.p. (°C.) |
|---|---|---|---|---|---|
| 303 | H | H | H | H | |
| 304 | H | H | 4'-F | H | oil |
| 305 | H | H | 3'-F | H | |
| 306 | H | H | 4'-Cl | H | |
| 307 | H | H | 3'-Cl | H | |
| 308 | H | H | 2'-F | H | |
| 309 | H | H | 2'-Cl | H | |
| 310 | H | H | 4'-CH$_3$ | H | |
| 311 | H | H | 3'-CH$_3$ | H | |
| 312 | H | H | 3'-CN | H | |
| 313 | H | H | 4'-OCH$_3$ | H | |
| 314 | H | H | 3'-CF$_3$ | H | |
| 315 | H | H | 4'-F | 3'-F | |
| 316 | H | H | 4'-Cl | 3'-F | |
| 317 | 5-F | H | 4'-F | H | |
| 318 | 6-F | H | 4'-Cl | H | |
| 319 | 7-F | H | H | H | |
| 320 | 6-Cl | H | H | H | |
| 321 | 6-CH$_3$ | H | 3'-F | H | |
| 322 | 5-OCH$_3$ | H | 4'-F | H | |
| 323 | 6-F | H | H | H | |
| 324 | 6-CH$_3$ | H | H | H | |
| 325 | H | H | 4'-CF$_3$ | H | |
| 326 | H | H | 3'-SCH$_3$ | H | |
| 327 | H | H | 4'-CN | H | |
| 328 | 6-Cl | 7-Cl | 3'-F | H | |
| 329 | 5-F | 7-F | H | H | |
| 330 | 6-F | 5-F | 4'-Cl | H | |

Formulations

Useful formulations of the compounds of Formulae I, II and III can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 7

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 6

Wettable Powder

| | |
|---|---|
| α,α-bis(4-chlorophenyl)-2-oxiranemethanol | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

Wettable Powder

| | |
|---|---|
| 2-[1-(4-chlorophenyl)-2-methylpropyl]oxirane | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

Granule

| | |
|---|---|
| Wettable Powder of Example 6 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 9

Extruded Pellet

| | |
|---|---|
| 2-[1-(4-chlorophenyl)-2-methylpropyl]oxirane | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). the granules held on a U.S.S. No. 40 sieve (0.42 mm openings) may be packaged for use and the fines recycled.

EXAMPLE 10

Oil Suspension

| | |
|---|---|
| α,α-bis(4-chlorophenyl)-2-oxiranemethanol | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

| | |
|---|---|
| 2-[1-(4-chlorophenyl)-2-methylpropyl]oxirane | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

| | |
|---|---|
| α,α-bis(4-chlorophenyl)-2-oxiranemethanol | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

| | |
|---|---|
| 2-[[(4,6-dimethoxypyrimidin-2-yl)amino-carbonyl]aminosulfonylmethyl]benzoic acid, methyl ester | 20% |
| α,α-bis(4-chlorophenyl)-2-oxiranemethanol | 20% |
| Polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Low Strength Granule

| | |
|---|---|
| 2-[1-(4-chlorophenyl)-2-methylpropyl]oxirane | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 15

Granule

| | |
|---|---|
| 2-[[(4,6-dimethoxypyrimidin-2-yl)amino-carbonyl]aminosulfonylmethyl]benzoic acid, methyl ester | 50% |
| α,α-bis(4-chlorophenyl)-2-oxiranemethanol | 30% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 16

High Strength Concentrate

| | |
|---|---|
| α,α-bis(4-chlorophenyl)-2-oxiranemethanol | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 17

Wettable Powder

| | |
|---|---|
| 2-[[(4,6-dimethoxypyrimidin-2-yl)amino-carbonyl]aminosulfonylmethyl]benzoic acid, methyl ester | 45% |
| α,α-bis(4-chlorophenyl)-2-oxiranemethanol | 45% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

Wettable Powder

| | |
|---|---|
| 2-[1-(4-chlorophenyl)-2-methylpropyl]oxirane | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

Oil Suspension

| | |
|---|---|
| 2-[[(4,6-dimethoxypyrimidin-2-yl)amino-carbonyl]aminosulfonylmethyl]benzoic acid, methyl ester | 26% |
| α,α-bis(4-chlorophenyl)-2-oxiranemethanol | 13% |
| blend of polyalcohol carboxylic esters and oil soluble petroleum sulfonates | 6% |
| xylene | 55% |

The ingredients are combined and ground together in a sand mill to produce particles essentially all below 5 microns. The product can be used directly, extended with oils, or emulsified in water.

EXAMPLE 20

Dust

| | |
|---|---|
| α,α-bis(4-chlorophenyl)-2-oxiranemethanol | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 21

Emulsifiable Concentrate

| | |
|---|---|
| 2-[1-(4-chlorophenyl)-2-methylpropyl]oxirane | 20% |
| chlorobenzene | 74% |
| sorbitan monostearate and polyoxyethylene condensates thereof | 6% |

The ingredients are combined and stirred to produce a solution which can be emulsified in water for application.

Utility

Compounds of this invention are particularly useful for the control of weeds in rice and may be used for both paddy and dryland rice. They may be applied post-emergence to dryland rice, to paddy rice or to rice from which the flood has been removed. The flood may be restored when the chemical has had time to penetrate the weeds. They may also be applied to paddy rice after transplanting as a spray or granule. The application may be made from 3 to 10 days after transplanting.

Rates of 30 to 2000 g/Ha will provide weed control. The compounds are particularly useful for the control of barnyardgrass (*Echinochloa crusgalli*), a pernicious weed in rice culture, but may also provide complete or partial control of other weeds, particularly gramineous weeds, in rice.

To broaden the spectrum of control, the compounds of this invention may be used in combination with other rice herbicides such as 2-chloro-2',6'-diethyl-N-(butoxymethyl)acetanilide (butachlor), and 2,4-dichlorophenoxyacetic acid (2,4-D).

In addition, compounds of this invention are useful for the control of weeds in cereal crops including wheat and barley. They are effective in both preemergence and postemergence applications. Superior results are obtained as preemergence treatments especially under conditions involving preplant incorporation of the herbicide into the soil.

Rates of 125 to 2000 g/ha will provide weed control. The compounds are particularly useful for the control of wild oats (*Avena fatua*), green foxtail (*Setaria viridis*), blackgrass (*Alopecurus myosuroides*), and annual ryegrass (*Lolium multiflorum*), but may also provide complete or partial control of other weeds in cereals.

TEST A

Seeds of crabgrass (Digitaria spp.), barnyard-grass (*Echinochloa crusgalli*), wild oats (*Avena fatua*), cheatgrass (*Bromus secalinus*), velvetleaf (*Abutilon theophrasti*), morningglory (Ipomoea spp.), cocklebur (*Xanthium pennsylvanicum*), sicklepod (*Cassia obtusifolia*), sorghum, corn, soybean, sugarbeet, cotton, rice, wheat and purple nutsedge (*Cyperus rotundus*) were planted and treated preemergence with the test chemicals dissolved in a non-phytotoxic solvent. At the same time, these crops and weed species were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| | Cmpd. 171 | Cmpd. 20 | | Cmpd. 21 | Cmpd. 22 | Cmpd. 32 | Cmpd. 2 | Cmpd. 174 | Cmpd. 26 | Cmpd. 1 | Cmpd. 24 | Cmpd. 51 | | Cmpd. 120 | Cmpd. 208 | Cmpd. 213 | Cmpd. 212 |
|---|---|---|---|---|---|---|---|---|---|---|---|---|---|---|---|---|---|
| Rate kg/ha | 2.0 | 2.0 | 0.4 | 2.0 | 2.0 | 2.0 | 2.0 | 0.4 | 2.0 | 2.0 | 2.0 | 2.0 | 0.4 | 1B,3G | 1B | 1B,4H | 1B,8G |
| | | | | | | | | POSTEMERGENCE | | | | | | | | | |
| Morningglory | 6B | 0 | 0 | 0 | 0 | 0 | 0 | 0 | 0 | 0 | 0 | 0 | 0 | 0 | 0 | 3G | 1H |
| Cocklebur | 0 | 0 | 0 | 0 | 0 | 0 | 0 | 0 | 0 | 0 | 0 | 4G | 2G | 9G | 4G | 8G | 0 |
| Nutsedge | 0 | 0 | 5G | 2G | 6H | 0 | 0 | 5H | 8H | 0 | 9G | 2G | 0 | 9G | 9G | 9G | 9G |
| Crabgrass | 1B,9H | 9H | 9H | 9H | 9H | 0 | 0 | 4H | 9H | 0 | 8H | 9H | 2G | 9H | 9H | 9H | 9H |
| Barnyardgrass | 1B,7G | 10H | 9H | 5H | 5H | 0 | 0 | 0 | 0 | 0 | 5G | 5G | 0 | 4G | 4H | 7G | 0 |
| Wild Oats | 1B | 10H | 9H | 0 | 0 | 0 | 0 | 0 | 0 | 1H | 0 | 0 | 0 | 7G | 0 | 9H | 0 |
| Wheat | 2B | 10H | 9H | 0 | 0 | 0 | 0 | 0 | 0 | 1H | 0 | 2G | 0 | 2G | 2H | 1B | 4H |
| Corn | 2B | 9H | 0 | 0 | 0 | 0 | 0 | 0 | 0 | 2G | 8G | 8G | 2G | 5G | 9G | 9G | 0 |
| Soybean | 1B | 10E | 10E | 6G | 3G | 0 | 0 | 0 | 0 | 0 | 6G | 2G | 0 | 7G | 2G | 5G | 9G |
| Rice | 2B | 10E | 9H | 0 | 0 | 0 | 0 | 0 | 0 | 0 | 0 | 5G | 0 | 5G | 2H | 5G | 0 |
| Sorghum | 2G | 3H | 0 | 0 | 0 | 0 | 0 | 0 | 0 | 0 | 3G | 8G | 0 | 8G | 0 | 5G | 1H |
| Sugar beet | 1B | 0 | 0 | 0 | 0 | 0 | 0 | 0 | 0 | 0 | 0 | 0 | 0 | 0 | 0 | 0 | 5G |
| Cotton | | 2G | 0 | 0 | 0 | 0 | 0 | 0 | 0 | 0 | 0 | 0 | 0 | 0 | 0 | 2G | 0 |
| Sicklepod | | 0 | 0 | 0 | 0 | 0 | 0 | 0 | 0 | 0 | 3G | 0 | 0 | 0 | 0 | 7G | 0 |
| Velvetleaf | | | | | | | | | | | | | | | | | |
| Cheat Grass | | | | | | | | | | | | | | | | | |

| | | | | | | | | | | | | | | | | | |
|---|---|---|---|---|---|---|---|---|---|---|---|---|---|---|---|---|---|
| | | | | | | | | PREEMERGENCE | | | | | | | | | |
| Morningglory | 6G | | | 3H | 0 | 0 | 0 | 4G | 0 | 3G | 0 | 0 | 0 | 9G | 2G | 5G | 5G |
| Cocklebur | — | | | — | 0 | 2G | 0 | — | 0 | — | — | 0 | 4G | 0 | 4G | 0 | 0 |
| Nutsedge | 8G | | | 2G | 2G | 0 | 5G | 9G | 5G | 10H | 5G | 0 | 0 | 10E | 5G | 10E | 0 |
| Crabgrass | 4G | | | 10H | 10H | 5G | 9H | 9G | 10E | 9H | 10H | 9H | 0 | 10E | 8H | 10H | 9H |
| Barnyardgrass | 9H | | | 10H | 10E | 9H | 6H | 9G | 10H | 10H | 10H | 9H | 0 | 10H | 9H | 9H | 9H |
| Wild Oats | 9H | | | 7G | 10H | 7H | 6H | 7G | 9H | 10H | 9H | 8G | 0 | 10H | 7G | 9H | 4G |
| Wheat | 8H | | | 10H | 6G | 9H | 9H | 3G | 10H | 9H | 10H | 8G | 0 | 5G | 8G | 9H | 6G |
| Corn | 7H | | | 9H | 9H | 3H | 9H | 0 | 9H | 10H | 10H | 0 | 0 | 9H | 8H | 9H | 2G |
| Soybean | 4G | | | 0 | 3G | 0 | 0 | 0 | 4G | 2H | 2H | 0 | 0 | 6G | 2H | 8G | 9H |
| Rice | 10E | | | 3G | 9H | 4G | 4G | 3G | 10E | 10E | 10E | 8H | 8H | 10E | 9H | 10E | 9H |
| Sorghum | 9H | | | 6G | 6H | 4G | 3G | 6G | 9H | 10H | 10H | 5G | 0 | 9H | 5G | 10H | 9H |
| Sugar beet | 7G | | | 0 | 2G | 7H | 0 | 0 | 0 | 0 | 0 | 0 | 0 | 10C | 4G | 5C,9G | 2H |
| Cotton | 3G | | | 0 | 0 | 4G | 0 | 0 | 2G | 0 | 0 | 0 | 0 | 6G | 0 | 7G | 0 |
| Sicklepod | 2G | | | 0 | 0 | 9G | 0 | 2G | 0 | 0 | 7G | 0 | 4G | 0 | 0 | 0 | 0 |
| Velvetleaf | | | | | | | | | | | | | | 8G | 2G | 5G | 4G |
| Cheat Grass | | | | | | | | | | | | | | 10E | 5G | 9H | 4G |

| | Cmpd. 214 | Cmpd. 121 | Cmpd. 175 | Cmpd. 173 | Cmpd. 169 | Cmpd. 117 | Cmpd. 168 | Cmpd. 275 | Cmpd. 281 | Cmpd. 276 | Cmpd. 278 | Cmpd. 251 | Cmpd. 253 | Cmpd. 193 |
|---|---|---|---|---|---|---|---|---|---|---|---|---|---|---|
| Rate kg/ha | 2.0 | 2.0 | 2.0 | 2.0 | 0.4 | 2.0 | 0.4 | 2.0 | 0.4 | 0.4 | 0.4 | 0.4 | 0.4 | 0.4 |
| | | | | | | POSTEMERGENCE | | | | | | | | |
| Morningglory | 1B,4G | 1B | 1B,2H | 0 | 7B | 4B | 0 | 2B | 0 | 2G | 1B | 0 | 0 | 4B |
| Cocklebur | 2G | 0 | 0 | 0 | 0 | 0 | 0 | 0 | 0 | 0 | 0 | 0 | 0 | 0 |
| Nutsedge | 5C,9G | 6G | 0 | 2C,9G | 0 | 0 | 0 | 2B,9G | 8G | 9H | 8G | 8H | 8H | 1B,8G |
| Crabgrass | 9G | 9G | 6G | 9H | 9H | 1B,8G | 1B,8G | 7B,9H | 9H | 9H | 7H | 5H | 8H | 3B,9H |
| Barnyardgrass | 9H | 9H | 7H | 0 | 0 | 3B,9H | 3B,9H | 1B | 0 | 8H | 7G | 0 | 0 | 1B |
| Wild Oats | 5H | 9H | 2H | 7H | 9H | 1B | 1B | 2B | 8G | 6G | 0 | 0 | 0 | 2B |
| Wheat | 8G | 3G | 2G | 0 | 0 | 2B | 2B | 0 | 3H | 6H | 0 | 0 | 0 | 2B |
| Corn | 9H | 9H | 0 | 3G | 0 | 3B | 3B | 1B | 0 | 4H | 0 | 0 | 0 | 3B |
| Soybean | 2H | 1H | 0 | 9H | 9H | 2B | 2B | 4G | 8G | 9G | 0 | 0 | 4G | 2B |
| Rice | 9G | 9G | 0 | 1B | 6H | 3B | 3B | 0 | 3G | 0 | 0 | 0 | 0 | 1B |
| Sorghum | 8H | 4G | 0 | 0 | 0 | 1B | 1B | 4H | 2G | 8H | 8H | 0 | 0 | 1B |
| Sugar beet | 4H | 3H | 0 | 2C,9H | 9G | 1B,4G | 1B,4G | 4H | 0 | 4H | 2H | 0 | 0 | 1B,4G |

TABLE A-continued

| | 6G | 5G | 0 | 0 | 0 | 0 | 0 | 4B,8G | 0 | 0 | 1H | 0 | 0 | 0 | 4B,8G |
|---|---|---|---|---|---|---|---|---|---|---|---|---|---|---|---|
| Cotton | 1C | 0 | 0 | 4G | 0 | 0 | — | — | — | — | — | — | — | — | 1B |
| Sicklepod | 9G | 3G | 0 | 0 | 0 | 0 | — | — | — | — | — | — | — | — | 1B |
| Velvetleaf | | | | | | | | | | | | | | | |
| Cheat Grass | | | | | | | | | | | | | | | |
| | | | | | | | PREEMERGENCE | | | | | | | |
| Morningglory | 9G | 8G | 0 | 0 | 0 | 3G | 0 | 0 | 9G | 0 | 9G | 0 | 0 | 0 | 0 |
| Cocklebur | 0 | 0 | 0 | 0 | 0 | 0 | 0 | 0 | 7G | 0 | 2G | 0 | 0 | 0 | 0 |
| Nutsedge | 4G | 5G | 0 | 0 | 5G | 5G | 0 | 0 | 0 | 10E | 2H | 0 | 0 | 0 | 0 |
| Crabgrass | 9H | 10H | 2H | 9H | 10E | 9H | 0 | 10H | 10H | 10E | 10E | 10E | 6G | 8H | 10H |
| Barnyardgrass | 10H | 10H | 9G | 9H | 0 | 9H | 0 | 10H | 10H | 7H | 10E | 10E | 10E | 9H | 10H |
| Wild Oats | 8G | 10H | 5G | 9H | 0 | 3G | 0 | 7G | 7G | 5H | 8G | 7G | 5G | 7G | 7G |
| Wheat | 8G | 8G | 2G | 7H | 0 | 2G | 0 | 6G | 5G | 0 | 10E | 6G | 6G | 3G | 6G |
| Corn | 9H | 9H | 0 | 0 | 0 | 0 | 0 | 2G | 2G | 0 | 5G | 2G | 2G | 0 | 2G |
| Soybean | 7G | 7G | 6G | 9H | 2G | 7G | 0 | 0 | 0 | 0 | 10E | 0 | 0 | 4G | 0 |
| Rice | 10E | 10E | 8G | 9H | 4G | 4G | 0 | 7G | 2G | 10H | 10E | 10H | 4G | 9H | 7G |
| Sorghum | 9H | 10H | 5G | 2G | 0 | 0 | 0 | 6G | 8H | 10H | 10E | 10H | 10H | 5G | 6G |
| Sugar beet | 8G | 10C | 0 | 0 | 0 | 3G | 0 | 5G | 7G | 3H | 10C | 3H | 7G | 3G | 5G |
| Cotton | 5G | 8G | 0 | 0 | 0 | 0 | 0 | 0 | 8G | 0 | 8G | 0 | 0 | 0 | 0 |
| Sicklepod | 5H | 5G | 0 | 0 | 0 | — | — | — | — | — | — | — | — | — | — |
| Velvetleaf | 10H | 10H | 4G | 5G | 0 | — | — | — | — | — | — | — | — | — | 0 |
| Cheat Grass | | | | | | | | | | | | | | | 3G |

TEST B

Sixteen-cm diameter Wagner pots, equipped with a stoppered drain opening near the bottom of the side wall, were filled with Woodstown sandy loam. About 1500 ml of water were added to each pot to bring the water level to a point 3 cm above the soil surface. Japonica and Indica rice seedlings were transplanted. Also, a number of barnyardgrass (*Echinochloa crusgalli*) seeds were added to each pot. At the same time, seedlings or tubers of the following species were transplanted into the muddy soil: water plaintain (*Alisma trivale*), Scirpus (*Scirpus mucranatus*), and Cyperus (*Cyperus difformis*). The weed species selected for this test are of economic importance in major rice-growing areas. The chemical treatments were applied within hours after transplanting two additional species: water chestnut (Eleocharis spp.) and arrowhead (*Sagittaria latifolia*). Shortly after treatment, the drain hold was opened to drop the water level by two cm. Water was then added to restore the water level to its original height. The following day the draining and refilling process was repeated. The pots were then maintained in the greenhouse. Rates of application and plant response ratings made 21 days after treatment are summarized in Table B. Note that Compound 171 alone effectively controls barnyardgrass and the combination of Compound 1 and 2-[[(4,6-dimethoxypyrimidin-2-yl)aminocarbonyl]aminosulfonylmethyl]benzoic acid, methyl ester controls a broad spectrum of rice weeds.

TABLE B

| Rate g/ha | R_J | R_I | BYG | WC | A | SC | CY | WP |
|---|---|---|---|---|---|---|---|---|
| With Treatment: | | | | | | | | |

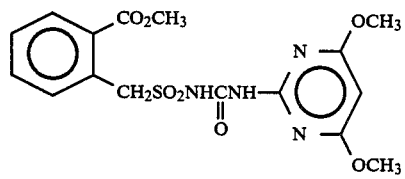

| 50 | 0 | 0 | 50 | 87 | 75 | 80 | 83 | 93 |
| 100 | 20 | 0 | 80 | 95 | 70 | 93 | 97 | 95 |
| 200 | 33 | 20 | 97 | 100 | 85 | 100 | 100 | 100 |
| 400 | 40 | 20 | 100 | 100 | 95 | 100 | 100 | 97 |
| With Treatment 171: | | | | | | | | |
| 50 | 0 | 0 | 50 | 0 | 0 | 0 | 0 | 0 |
| 75 | 0 | 0 | 85 | 0 | 0 | 0 | 0 | 0 |
| 100 | 0 | 0 | 95 | 0 | 0 | 0 | 0 | 0 |
| With Treatment 171 and: | | | | | | | | |

$$\text{structure: benzene ring with } CO_2CH_3 \text{ and } CH_2SO_2NHCNH\text{(C=O)}-\text{pyrimidine with two } OCH_3$$

| 50 + 50 | 0 | 0 | 95 | 95 | 60 | 95 | 97 | 100 |
| 50 + 75 | 0 | 0 | 95 | 95 | 68 | 90 | 80 | 85 |
| 50 + 100 | 0 | 10 | 100 | 97 | 75 | 85 | 90 | 85 |
| 100 + 50 | 10 | 7 | 95 | 100 | 90 | 85 | 90 | 100 |
| 100 + 75 | 0 | 0 | 97 | 100 | 85 | 90 | 95 | 100 |
| 100 + 100 | 20 | 20 | 100 | 100 | 85 | 93 | 93 | 100 |
| 200 + 50 | 20 | 20 | 100 | 100 | 85 | 87 | 97 | 95 |
| 200 + 75 | 20 | 20 | 97 | 100 | 85 | 93 | 100 | 100 |
| 200 + 100 | 20 | 20 | 100 | 100 | 97 | 100 | 95 | 95 |
| 400 + 50 | 30 | 0 | 100 | 100 | 100 | 100 | 100 | 100 |
| 400 + 75 | 25 | 20 | 100 | 100 | 100 | 100 | 100 | 100 |
| 400 + 100 | 23 | 20 | 100 | 100 | 100 | 100 | 100 | 100 |

R_J = Japonica Rice
R_I = Indica Rice
BYG = Barnyardgrass
WC = Waterchestnut
A = Arrowhead
SC = Scirpus
CY = Cyperus
WP = Water Plaintain

TEST C

Barnyardgrass seed was sown into 12 cm diameter wax cups containing Sassafras sandy loam soil, which was kept moist but not flooded until seedlings began to emerge. At that time, rice (Japonica and Indica varieties) was transplanted into similar cups when the rice was at the 2–3 leaf stage. A permanent flood was established 4 or 5 days following transplanting the rice. Both the rice and barnyardgrass were flooded 3.0 cm deep.

Following the flood, compounds were applied directly to the paddy after being formulated in a non-phytotoxic solvent.

Rice growth and barnyardgrass control were evaluated approximately 17 days following compound application. Rice injury was evaluated by analysis of seedling fresh weight and converted to % injury relative to untreated plants. Barnyardgrass control was visually determined using a scale of 0 to 100% (0=no control; 100=complete control). Each treatment was replicated twice. The results are summarized in Table C.

TABLE C

Barnyardgrass Control and Rice Tolerance

| Compound Number | Rate (g/ha) | % Control or Injury Barnyardgrass | Rice (Japonica/Indica) |
|---|---|---|---|
| 171 | 0.25 | 0 | 0/0 |
|  | 1 | 0 | 0/0 |
|  | 4 | 0 | 0/0 |
|  | 16 | 23 | 0/0 |
|  | 63 | 63 | 0/0 |
|  | 250 | 93 | 0/0 |
|  | 1000 | 100 | 0/0 |
| 21 | 0.25 | 0 | 10/20 |
|  | 1 | 0 | 0/0 |
|  | 4 | 0 | 0/0 |
|  | 16 | 0 | 0/0 |
|  | 63 | 40 | 10/10 |
|  | 250 | 95 | 0/20 |
|  | 1000 | 100 | 20/0 |
| 1 | 0.25 | 0 | 0/0 |
|  | 1 | 0 | 0/0 |
|  | 4 | 0 | 0/0 |
|  | 16 | 0 | 0/0 |
|  | 63 | 17 | 0/0 |
|  | 250 | 65 | 0/0 |
|  | 1000 | 97 | 0/55 |
| 166 | 0.25 | 0 | 0/0 |
|  | 1 | 0 | 0/0 |
|  | 4 | 0 | 0/0 |
|  | 16 | 0 | 0/0 |
|  | 64 | 72 | 0/0 |
|  | 250 | 100 | 0/0 |
|  | 1000 | 100 | 20/0 |
| 104 | 0.25 | 0 | 0/0 |
|  | 1 | 0 | 0/0 |
|  | 4 | 0 | 0/0 |
|  | 16 | 0 | 0/0 |
|  | 64 | 33 | 0/0 |

TABLE C-continued

Barnyardgrass Control and Rice Tolerance

| Compound Number | Rate (g/ha) | Barnyardgrass % Control | Rice (Japonica/Indica) % Injury |
|---|---|---|---|
|  | 250 | 100 | 0/0 |
|  | 1000 | 100 | 0/0 |
| 106 | 0.25 | 0 | 0/0 |
|  | 1 | 0 | 0/0 |
|  | 4 | 0 | 0/0 |
|  | 16 | 0 | 0/0 |
|  | 64 | 50 | 0/0 |
|  | 250 | 100 | 0/0 |
|  | 1000 | 100 | 0/0 |
| 275 | 0.25 | 0 | 0/0 |
|  | 1 | 0 | 0/0 |
|  | 4 | 0 | 0/0 |
|  | 16 | 0 | 0/0 |
|  | 64 | 25 | 20/0 |
|  | 250 | 100 | 0/0 |
|  | 1000 | 100 | 0/0 |
| 276 | 0.25 | — | 25/0 |
|  | 1 | — | 20/0 |
|  | 4 | — | 0/0 |
|  | 16 | — | 0/40 |
|  | 30 | 74 | — |
|  | 64 | 98 | 0/0 |
|  | 125 | 99 | — |
|  | 250 | 100 | 0/25 |
|  | 1000 | 100 | 35/70 |

TEST D

Pre-germinated Indica rice (*Oryza sativa*) seeds are sown into Wagner pots containing wet Sassafras sandy loam soil. Seeds of barnyardgrass (*Echinochloa crusgalli*) and hemp sesbania (*Sesbania exaltata*) are sown into additional Wagner pots. Compounds, formulated in a non-phytotoxic solvent, are applied directly to the Wagner pots either prior to establishing a permanent flood or shortly thereafter. Application of compounds is normally 3 to 12 days after seeding. Evaluation is conducted 21 to 25 days after treatment. Ratings are in % weed control or rice injury, visually assessed, relative to untreated controls. The results are summarized in Table D.

TABLE D

| Treatment | Rate g/ha | Preemergence R | Preemergence BYG | Preemergence SES | Postemergence R | Postemergence BYG | Postemergence SES |
|---|---|---|---|---|---|---|---|
| 171 | 63 | 60 | 0 | 0 | 0 | 0 | 0 |
|  | 125 | 87 | 40 | 0 | 0 | 33 | 0 |
|  | 250 | 100 | 75 | 0 | 42 | 60 | 0 |
|  | 500 | 100 | 97 | 0 | 70 | 80 | 0 |

R = Indica Rice
BYG = Barnyardgrass
SES = Hemp Sesbania

TEST E

Seeds of rice (*Oryza sativa*), barnyardgrass (*Echinochloa crusgalli*), morningglory (*Ipomoea purpurea*), wild oats (*Avena fatua*), nutsedge (*Cyperus esculentus*) and crabgrass (*Digitaria ischaemum*) are sown into 25 cm diameter plastic pots containing Sassafras sandy loam soil. Compounds, formulated in a non-phytotoxic solvent, are applied as preemergence and postemergence (rice=2 to 3 leaves) treatments. Evaluation, by visual assessment, is conducted 21 to 25 days following treatment. Weed control and rice injury ratings are based on a % system relative to the untreated controls. The results are summarized in Table E.

TABLE E

| Treatment | Rate g/ha | R | BYG | NS | MG | WO | C |
|---|---|---|---|---|---|---|---|
| 171 (post) | 125 | 0 | 0 | 0 | 0 | 0 | 0 |
|  | 250 | 0 | 0 | 0 | 0 | 0 | 0 |
|  | 500 | 0 | 70 | 0 | 0 | 0 | 40 |
|  | 1000 | 0 | 80 | 0 | 0 | 0 | 50 |
| 171 (pre) | 125 | 0 | 0 | 0 | 0 | 0 | 0 |
|  | 250 | 0 | 90 | 0 | 0 | 0 | 0 |
|  | 500 | 0 | 95 | 0 | 0 | 0 | 65 |
|  | 1000 | 0 | 95 | 0 | 0 | 0 | 85 |

R = Rice
BYG = Barnyardgrass
NS = Nutsedge
MG = Morningglory
WO = Wild Oats
C = Crabgrass

TEST F

Postemergence

Two round pans (25 cm diameter by 12.5 cm deep) were filled with Sassafras sandy loam soil. One pan was planted with blackgrass (*Alopecurus myosuroides*), sugar beets, nutsedge (*Cyperus rotundus*) tubers, rape (*Brassica napus*), crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Preemergence

Two round pans (25 cm diameter by 12.5 cm deep) were filled with Sassafras sandy loam soil. One pan was planted with weed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 100 where 0=no effect and 100=complete control. Some compounds were rated using a scale where 0=no injury and 10=complete control; G=growth retardation. A dash (-) response means no test.

Response ratings are contained in Table F.

TABLE F

POSTEMERGENCE

| | Cmpd. 20 | | | Cmpd. 21 | | | Cmpd. 22 | | | Cmpd. 26 | | Cmpd. 24 | | Cmpd. 51 | | Cmpd. 118 | | | Cmpd. 114 | | Cmpd. 78 | | Cmpd. 115 | | |
|---|---|---|---|---|---|---|---|---|---|---|---|---|---|---|---|---|---|---|---|---|---|---|---|---|---|
| Rate g/ha | 1000 | 250 | 1000 | 250 | 62 | 4000 | 1000 | 250 | 1000 | 250 | 1000 | 1000 | 250 | 1000 | 250 | 1000 | 250 | 62 | 1000 | 250 | 1000 | 250 | 1000 | 250 | 62 |
| Corn | 0 | 0 | 0 | 0 | 0 | 2G | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 40 |
| Rice | 0 | 0 | 6G | 2G | 0 | 5G | 5G | 0 | 0 | 0 | 0 | 0 | 0 | 20 | 0 | 0 | 0 | 0 | 40 | 0 | 50 | 0 | 20 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 2G | 2G | 0 | 0 | 0 | 0 | 0 | 0 | 40 | 30 | 0 | 0 | 0 | 0 | 0 | 30 | 0 | 20 | 0 | 0 |
| Sugar beet | 0 | 0 | 0 | 0 | 0 | 0 | 0 | 0 | 0 | 0 | 20 | 0 | 0 | 20 | 0 | 0 | 0 | 0 | 0 | 0 | 30 | 0 | 0 | 0 | 0 |
| Rape | — | — | — | — | — | — | — | — | — | — | 20 | 0 | 0 | 40 | 30 | 0 | 0 | 0 | 0 | 0 | 0 | 0 | 0 | 0 | 0 |
| Crabgrass | 0 | 0 | 7G | 3G | 0 | 8G | 9G | 2G | 7G | 2G | 0 | 0 | 0 | 20 | 0 | 80 | 30 | 0 | 80 | 0 | 100 | 90 | 100 | 50 | 30 |
| Johnsongrass | 0 | 0 | 0 | 2G | 0 | 7G | 8G | 2G | 0 | 2G | 0 | 70 | 20 | 90 | 0 | 40 | 0 | 30 | 70 | 70 | 70 | 60 | 100 | 30 | 0 |
| Blackgrass | 0 | 0 | 3G | 0 | 0 | 5G | 6G | 0 | 0 | 0 | 0 | 0 | 0 | 90 | 30 | 80 | 30 | 30 | 80 | 50 | 50 | 40 | 100 | 0 | 0 |
| Barnyardgrass | 0 | 0 | 7G | 5G | 0 | 9G | 7G | 2G | 0 | 2G | 0 | 0 | 0 | 90 | 30 | 30 | 0 | 40 | 100 | 100 | 100 | 70 | 90 | 30 | 0 |
| Nutsedge | 0 | 0 | 0 | 0 | 0 | 5G | 5G | 0 | 0 | 0 | 0 | 0 | 0 | 30 | 0 | 0 | 0 | 0 | 0 | 0 | 0 | 0 | 0 | 0 | 60 |
| Giant Foxtail | 0 | 0 | 0 | 0 | 0 | 6G | 6G | 4G | 0 | 3G | 0 | 20 | 0 | 80 | 30 | 60 | 0 | 40 | 70 | 0 | 90 | 0 | 90 | 40 | 0 |
| Wild Oats | 0 | 0 | 0 | 7G | 0 | 7G | 7G | 0 | 0 | 0 | 0 | 30 | 0 | 20 | 20 | 30 | 0 | 30 | 0 | 20 | 20 | 0 | 20 | 0 | 0 |
| Cocklebur | 2G | 0 | 0 | 0 | 0 | 0 | 0 | 0 | 0 | 0 | 0 | 50 | 0 | 20 | 0 | 30 | 0 | 0 | 50 | 0 | 30 | 0 | 30 | 0 | 0 |
| Morningglory | 0 | 0 | 0 | 0 | 0 | 0 | 0 | 0 | 0 | 0 | 0 | 40 | 20 | 30 | 20 | 80 | 0 | 30 | 0 | 0 | 30 | 0 | 60 | 0 | 0 |
| Teaweed | 0 | 0 | 2G | 0 | 0 | 2G | 2G | 0 | 0 | 0 | 0 | 20 | 0 | 0 | 20 | 0 | 0 | 0 | 30 | 0 | 30 | 0 | 30 | 0 | 0 |
| Sicklepod | 0 | 0 | 0 | 0 | 0 | 3G | 3G | 0 | 0 | 0 | 0 | 0 | 0 | 20 | 20 | 0 | 0 | 0 | 0 | 0 | 20 | 30 | 0 | 0 | 0 |
| Jimsonweed | 4G | 0 | 0 | 0 | 0 | 0 | 0 | 0 | 0 | 0 | 0 | 30 | 0 | 20 | 0 | 30 | 0 | 0 | 60 | 0 | 60 | 0 | 60 | 0 | 0 |
| Velvetleaf | 3G | 0 | 0 | 0 | 0 | 2G | 2G | 0 | 2G | 0 | 2G | 0 | 0 | 0 | 0 | 0 | 0 | 0 | 0 | 0 | 0 | 0 | 30 | 0 | 0 |

PREEMERGENCE

| | Cmpd. 115 | | Cmpd. 51 | | Cmpd. 118 | | | Cmpd. 114 | | Cmpd. 280 | | Cmpd. 276 | | Cmpd. 278 | | Cmpd. 246 | | |
|---|---|---|---|---|---|---|---|---|---|---|---|---|---|---|---|---|---|---|
| Rate g/ha | 1000 | 250 | 1000 | 250 | 1000 | 250 | 62 | 1000 | 250 | 1000 | 250 | 1000 | 250 | 1000 | 250 | 1000 | 250 | 62 |
| Corn | 0 | 0 | 30 | 0 | 0 | 0 | 0 | 60 | 0 | 0 | 0 | 60 | 30 | 0 | 0 | 0 | 0 | 0 |
| Wheat | 0 | 0 | 100 | 40 | 100 | 70 | 30 | 90 | 50 | 60 | 0 | 90 | 0 | 70 | 40 | 20 | 20 | 50 |
| Rice | 0 | 0 | 0 | 0 | 60 | 100 | 30 | 0 | 100 | 100 | 100 | 100 | 0 | 30 | 0 | 100 | 100 | 0 |
| Soybean | 0 | 0 | 100 | 40 | 60 | 60 | 30 | 70 | 60 | 100 | 70 | 100 | 0 | 100 | 70 | 60 | 60 | 0 |
| Cotton | 0 | 0 | 20 | 0 | 80 | 80 | 40 | 60 | 0 | 70 | 50 | 100 | 0 | 100 | 50 | 60 | 90 | 30 |
| Sugar beet | 0 | 0 | 100 | 30 | 80 | 70 | 40 | 90 | 40 | 100 | 90 | 100 | 0 | 0 | 30 | 50 | 100 | 50 |
| Rape | 0 | 0 | 30 | 0 | 70 | 30 | 30 | 0 | 0 | 20 | 0 | 30 | 0 | 70 | 0 | 0 | 0 | 40 |
| Crabgrass | 30 | 0 | 100 | 40 | 0 | 30 | 0 | 30 | 0 | 100 | 100 | 30 | 0 | 100 | 90 | 20 | 30 | 100 |
| Johnsongrass | 100 | 0 | 100 | 40 | 100 | 100 | 70 | 100 | 70 | 100 | 20 | 100 | 0 | 100 | 80 | 60 | 100 | 20 |
| Blackgrass | 0 | 0 | 20 | 30 | 60 | 60 | 30 | 70 | 60 | 70 | 0 | 100 | 0 | 90 | 90 | 60 | 60 | 30 |
| Barnyardgrass | 20 | 0 | 100 | 0 | 80 | 80 | 40 | 60 | 90 | 100 | 20 | 100 | 50 | 0 | 100 | 60 | 100 | 50 |
| Nutsedge | 100 | 0 | 30 | 0 | 50 | 30 | 0 | 50 | 0 | 20 | 0 | 50 | 0 | 70 | 30 | 50 | 0 | 40 |
| Giant Foxtail | 30 | 0 | 100 | 40 | 100 | 70 | 50 | 100 | 40 | 100 | 20 | 100 | 0 | 100 | 100 | 70 | 100 | 0 |
| Wild Oats | 0 | 0 | 30 | 0 | 90 | 0 | 0 | 90 | 0 | 0 | 0 | 90 | 0 | 80 | 30 | 60 | 60 | 0 |
| Cocklebur | 0 | 0 | 0 | 0 | 30 | 30 | 0 | 30 | 0 | 20 | 0 | 30 | 0 | 0 | 0 | 0 | 0 | 0 |
| Morningglory | 0 | 0 | 0 | 0 | 0 | 0 | 0 | 0 | 0 | 20 | 0 | 30 | 0 | 30 | 30 | 30 | 30 | 0 |
| Teaweed | 0 | 0 | 20 | 20 | 80 | 20 | 30 | 80 | 0 | 40 | 0 | 30 | 0 | 50 | 0 | 30 | 60 | 0 |
| Sicklepod | 2G | 0 | 0 | 20 | 0 | 20 | 0 | 0 | 70 | 30 | 0 | 30 | 0 | 20 | 30 | 50 | 30 | 0 |
| Jimsonweed | 0 | 0 | 30 | 20 | 60 | 20 | 30 | 60 | 0 | 60 | 20 | 0 | 0 | 30 | 0 | 20 | 60 | 0 |
| Velvetleaf | 2G | 0 | 0 | 30 | 0 | 30 | 0 | 30 | 0 | 20 | 0 | 0 | 0 | 0 | 0 | 0 | 20 | 0 |

POSTEMERGENCE

| | Cmpd. 115 | | Cmpd. 276 | | Cmpd. 278 | | Cmpd. 246 | |
|---|---|---|---|---|---|---|---|---|
| Rate g/ha | 62 | 1000 | 250 | 1000 | 250 | 1000 | 250 | 1000 | 62 |
| Corn | 0 | 0 | 50 | 0 | 0 | 0 | 0 | 0 | 0 |
| Wheat | 0 | 0 | 0 | 0 | 0 | 0 | 0 | 0 | 0 |

TABLE F-continued

| | | | | | | | | | |
|---|---|---|---|---|---|---|---|---|---|
| Rice | 0 | 0 | 0 | 0 | 0 | 0 | 0 | 0 | 0 |
| Soybean | 60 | 0 | 0 | 50 | 0 | 0 | 0 | 0 | 0 |
| Cotton | 0 | 0 | 0 | 0 | 0 | 0 | 0 | 0 | 0 |
| Sugar beet | 0 | 0 | 0 | 0 | 0 | 30 | 0 | 0 | 0 |
| Rape | 20 | 20 | 90 | 90 | 0 | 0 | 0 | 0 | 0 |
| Crabgrass | 0 | 90 | 0 | 40 | 70 | 0 | 80 | 40 | 40 |
| Johnsongrass | 0 | 0 | 20 | 40 | 0 | 50 | 50 | 0 | 0 |
| Blackgrass | 80 | 80 | 0 | 50 | 0 | 0 | 30 | 0 | 0 |
| Barnyardgrass | 90 | 0 | 0 | 80 | 70 | 0 | 0 | 0 | 0 |
| Nutsedge | 20 | 60 | 0 | 40 | 0 | 0 | 60 | 0 | 0 |
| Giant Foxtail | 60 | 20 | 0 | 0 | 0 | 0 | 30 | 0 | 0 |
| Wild Oats | 20 | 0 | 0 | 30 | 0 | 0 | 40 | 0 | 0 |
| Cocklebur | 0 | 20 | 0 | 30 | 0 | 30 | 50 | 30 | 30 |
| Morningglory | 20 | 40 | 20 | 0 | 30 | 0 | 50 | 30 | 0 |
| Teaweed | 40 | 20 | 0 | 50 | 30 | 0 | 60 | 30 | 0 |
| Sicklepod | 20 | 50 | 20 | 50 | 50 | 30 | 50 | — | 0 |
| Jimsonweed | 50 | 20 | 0 | 0 | 30 | 0 | 30 | 30 | 30 |
| Velvetleaf | 20 | 0 | 0 | 0 | 0 | 0 | 30 | 30 | 30 |

| | | | PREEMERGENCE | | | | | | |
|---|---|---|---|---|---|---|---|---|---|
| Rate g/ha | 1000 | 250 | 62 | 1000 | 250 | 62 | 1000 | 250 | 62 |
| Corn | 0 | 0 | 0 | 0 | 0 | 0 | 0 | 0 | 0 |
| Wheat | 30 | 0 | 0 | 0 | 0 | 0 | 60 | 30 | 0 |
| Rice | 90 | 30 | 0 | 0 | 0 | 0 | 80 | 0 | 0 |
| Soybean | 0 | 0 | 0 | 0 | 0 | 0 | 0 | 0 | 0 |
| Cotton | 0 | 0 | 0 | 0 | 0 | 0 | 0 | 0 | 0 |
| Sugar beet | 90 | 50 | 30 | 30 | 0 | 0 | 90 | 50 | 0 |
| Rape | 40 | 0 | 0 | 30 | 0 | 0 | 0 | 0 | 0 |
| Crabgrass | 100 | 90 | 70 | 100 | 70 | 60 | 100 | 90 | 70 |
| Johnsongrass | 100 | 90 | 50 | 100 | 60 | 40 | 60 | 0 | 0 |
| Blackgrass | 90 | 50 | 0 | 70 | 30 | 0 | 70 | 0 | 0 |
| Barnyardgrass | 100 | 100 | 50 | 100 | 70 | 90 | 80 | 0 | 0 |
| Nutsedge | 100 | 90 | 70 | 0 | 0 | 0 | 30 | 0 | 0 |
| Giant Foxtail | 100 | 100 | 60 | 100 | 90 | 60 | 80 | 70 | 50 |
| Wild Oats | 30 | 0 | 0 | 70 | 0 | 0 | 30 | 40 | 0 |
| Cocklebur | 70 | 50 | 30 | 40 | 0 | 0 | 50 | 30 | 0 |
| Morningglory | 50 | 30 | 30 | 0 | 0 | 0 | 50 | 30 | 0 |
| Teaweed | 50 | 30 | 0 | 50 | 30 | 0 | 30 | 30 | 0 |
| Sicklepod | 50 | 30 | — | 50 | 30 | — | — | — | — |
| Jimsonweed | 50 | 30 | 0 | 50 | 30 | 0 | 50 | 30 | 50 |
| Velvetleaf | 50 | 30 | 0 | 50 | 30 | 0 | 50 | 30 | 0 |

TEST G

Sixteen Wagner pots were filled with Anakida clay loam. About 1500 ml of water was added to each pot to bring the water level to a point 1 cm above the soil surface. Japonica rice (cultivar "Nihonbare") seedlings at the 2.2–2.5 leaf-stage were transplanted. At the same time, plastic pots (11.4 cm diameter) were filled with Anakida clay loam, watered to 1 cm above the soil and a number of barnyardgrass (*Echinochloa oryzicola*) seeds were sowed.

The chemical treatments were applied to rice three to four days after transplanting, and at the 0.5 leaf-stage and the 1.5 leaf-stage to barnyardgrass after adding water to bring the water level to a point 3 cm above the soil surface. The water level in all test pots was maintained thereafter at the same level by adding water when necessary. The pots were maintained in a greenhouse. Tested chemical, rates of application, and plant response ratings made 14 days or 21 days after treatment are summarized in Table G. The ratings are based on a numerical scale extending from 0=no injury, to 10=complete kill.

TABLE G

Barnyardgrass Control and Rice Tolerance

| Compound | Rate (g/ha) | Barnyardgrass Control 0.5 LS | 1.5 LS | Rice Injury |
|---|---|---|---|---|
| 78 | 32 | 0 | 0 | 1.5 |
|  | 64 | 7 | 0 | 1 |
|  | 125 | 10 | 3 | 1 |
|  | 250 | 10 | 5 | 2 |
| 168 | 125 | 5 | 0 | 1.5 |
|  | 250 | 10 | 0 | 1 |
|  | 500 | 10 | 3 | 0 |
|  | 1000 | 10 | 5 | 0.5 |
| 106 | 125 | 0 | 0 | 0 |
|  | 250 | 9 | 3 | 0.5 |
|  | 500 | 10 | 8 | 0 |
|  | 1000 | 10 | 10 | 0.5 |
| 193 | 125 | 5 | 0 | 1.5 |
|  | 250 | 10 | 0 | 1 |
|  | 500 | 10 | 3 | 0 |
|  | 1000 | 10 | 5 | 0.5 |

TEST H

Two evaluations were conducted. In the first evaluation, plastic trays were lined with polyethylene liners are filled with pasteurized Sassafras sandy loam soil (pH 6.5, 1% O.M.). One tray was planted with wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), annual ryegrass (*Lolium multiflorum*), and rapeseed (*Brassica napus*). A second tray was planted with *Matricaria inodora*, cleavers bedstraw (*Galium aparine*), Russian thistle (*Salsola kali*), shepherdspurse (*Capsella bursapastoris*), kochia (*Kochia scoparia*), black nightshade (*Solanum nigrum*), speedwell (*Veronica persica*), wild buckwheat (*Polygonum convolvulus*) and sugarbeet (*Beta vulgaris*). For postemergence treatments, the first tray was planted 14 days before spraying, and the second tray was planted 22 days before treatment. Plants in the postemergence treatments ranged in height from 1 to 15 cm, depending on species. Wheat, barley and wild oats were in the 2-leaf stage of development (Zadoks stage 11). A second set of trays were prepared in an identical manner before spraying to serve as preemergence treatments.

The herbicide was diluted in a nonphytotoxic solvent and applied to the trays using a belt sprayer. Plants were grown in a greenhouse for 21 days at which time visual ratings were made by comparing to an untreated control treatment. Ratings were based on a scale of 0=no effect to 100=complete kill. The results are summarized in Table H.

The second evaluation consisted of two 25 cm pans filled with either Sassafras sandy loam soil or Tama silt loam soil (pH 5.5, 3% O.M.). The first pot was prepared and seeded before herbicide treatment with wheat, barley, wild oats, cheatgrass, blackgrass, annual bluegrass, green foxtail, annual ryegrass, rapeseed and sugarbeet. The second pot was covered with a polyethylene bag and the soil used to cover the seed was added. This soil was then treated with the herbicide and thoroughly mixed. The seeds were then placed in the pot and covered with the treated soil. Plants were grown and evaluated in the manner previously described. The results are summarized in Tables I and J.

TABLE H

Plant Response Ratings for the Wheat and Barley Herbicide Screen

| Test Plant | Compound 120 Rate (g/ha) | | | | |
|---|---|---|---|---|---|
|  | 2000 | 1000 | 500 | 250 | 125 |
| *Preemergence* | | | | | |
| Wheat | 40 | 0 | 0 | 0 | 0 |
| Barley | 50 | 0 | 0 | 0 | 0 |
| Sugarbeets | 80 | 80 | 80 | 50 | 0 |
| Rapeseed | 30 | 10 | 0 | 0 | 0 |
| Wild Oats | 80 | 60 | 40 | 20 | 0 |
| Cheatgrass | 30 | 20 | 20 | 0 | 0 |
| Blackgrass | 60 | 30 | 30 | 0 | 0 |
| Annual Bluegrass | 70 | 30 | 30 | 10 | 0 |
| Green Foxtail | 100 | 90 | 80 | 30 | 20 |
| Italian Ryegrass | 100 | 90 | 60 | 20 | 0 |
| *Matricaria inodora* | 20 | 10 | 0 | 0 | 0 |
| *Galium aparine* | 30 | 0 | 0 | 0 | 0 |
| Russian Thistle | 30 | 20 | 0 | 0 | 0 |
| Shepherdspurse | 40 | 0 | 0 | 0 | 0 |
| Kochia | 60 | 50 | 50 | 0 | 0 |
| Black Nightshade | 30 | 0 | 0 | 0 | 0 |
| Speedwell | 60 | 0 | 0 | 0 | 0 |
| Wild Buckwheat | 0 | 0 | 0 | 0 | 0 |
| *Postemergence* | | | | | |
| Wheat | 20 | 0 | 0 | 0 | 0 |
| Barley | 60 | 50 | 20 | 20 | 0 |
| Sugarbeets | 30 | 0 | 0 | 0 | 0 |
| Rapeseed | 0 | 0 | 0 | 0 | 0 |
| Wild Oats | 60 | 50 | 20 | 20 | 0 |
| Cheatgrass | 30 | 0 | 0 | 0 | 0 |
| Blackgrass | 80 | 80 | 60 | 60 | 40 |
| Annual Bluegrass | 30 | 20 | 0 | 0 | 0 |
| Green Foxtail | 70 | 50 | 50 | 50 | 20 |
| Italian Ryegrass | 60 | 40 | 40 | 0 | 0 |
| *Matricaria inodora* | 0 | 0 | 0 | 0 | 0 |
| *Galium aparine* | 60 | 20 | 0 | 0 | 0 |
| Russian Thistle | 0 | 0 | 0 | 0 | 0 |
| Shepherdspurse | 0 | 0 | 0 | 0 | 0 |
| Kochia | 40 | 10 | 10 | 0 | 0 |
| Black Nightshade | 20 | 0 | 0 | 0 | 0 |
| SpeedWell | 40 | 40 | 40 | 10 | 0 |
| Wild Buckwheat | 0 | 0 | 0 | 0 | 0 |

TABLE 1

Plant Response Ratings for the Application Preemergence and Preplant Incorporated in Sassafras Sandy Loam Soil Compound 120

| | Preemergence | | | | Preplant Incorporated | | | |
|---|---|---|---|---|---|---|---|---|
| | Rate (g/ha) | | | | | | | |
| Species | 2000 | 1000 | 500 | 250 | 2000 | 1000 | 500 | 250 |
| Wheat | 10 | 0 | 0 | 0 | 35 | 10 | 0 | 0 |
| Barley | 10 | 0 | 0 | 0 | 60 | 50 | 40 | 0 |
| Sugarbeet | 75 | 60 | 40 | 0 | 85 | 70 | 65 | 30 |
| Rapeseed | 30 | 20 | 0 | 0 | 60 | 40 | 20 | 0 |
| Wild Oats | 98 | 60 | 40 | 10 | 100 | 100 | 98 | 75 |
| Cheatgrass | 20 | 0 | 0 | 0 | 98 | 90 | 85 | 20 |
| Blackgrass | 95 | 80 | 80 | 80 | 98 | 90 | 70 | 50 |
| Annual Bluegrass | 50 | 10 | 0 | 0 | 95 | 85 | 80 | 20 |
| Green Foxtail | 95 | 90 | 90 | 70 | 98 | 95 | 75 | 65 |
| Annual Ryegrass | 95 | 70 | 20 | 0 | 100 | 100 | 98 | 80 |

TABLE J

Plant Response Ratings for the Application Preemergence and Preplant Incorporated in Tama Silt Loam Soil Compound 120

| | Preemergence | | | | Preplant Incorporated | | | |
|---|---|---|---|---|---|---|---|---|
| | Rate (g/ha) | | | | | | | |
| Species | 2000 | 1000 | 500 | 250 | 2000 | 1000 | 500 | 250 |
| Wheat | 0 | 0 | 0 | 0 | 20 | 20 | 0 | 0 |
| Barley | 0 | 0 | 0 | 0 | 60 | 20 | 0 | 0 |
| Sugarbeet | 50 | 0 | 0 | 0 | 60 | 60 | 30 | 0 |
| Rapeseed | 30 | 0 | 0 | 0 | 60 | 35 | 10 | 0 |
| Wild Oats | 30 | 0 | 0 | 0 | 100 | 95 | 95 | 40 |
| Cheatgrass | 20 | 0 | 0 | 0 | 90 | 90 | 50 | 20 |
| Blackgrass | 100 | 90 | 90 | 80 | 95 | 90 | 50 | 50 |
| Annual Bluegrass | 40 | 20 | 0 | 0 | 100 | 95 | 40 | 0 |
| Green Foxtail | 95 | 95 | 80 | 30 | 100 | 90 | 90 | 60 |
| Annual Ryegrass | 75 | 20 | 0 | 0 | 100 | 100 | 90 | 20 |

What is claimed is:

1. Compounds of the formula $$R^2-\underset{\underset{X}{|}}{\overset{\overset{R^1}{|}}{C}}CH-\overset{O}{\overset{/\backslash}{\phantom{C}}}CH_2 \qquad I$$

wherein $R^1$ is

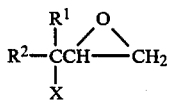

$R^2$ is $C_2$-$C_4$ alkyl, $C_3$-$C_6$ cycloalkyl, or

where $R^3$, $R^4$, $R_1^3$ and $R_1^4$ are independently H, F, Cl, Br, $CF_3$, CN, $NO_2$, $OCH_2CH_2OCH_3$, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio; and X is F, $CH_3$, or $OR^6$;

where $R^6$ is H, $C_1$-$C_3$ alkyl, $C(O)CH_3$ or $C(O)NHCH_3$.

2. The compounds of claim 1 wherein X is $OR^6$.

3. The compounds of claim 1 where $R^3$, $R^4$, $R_1^3$ and $R_1^4$ are independently H, F, Cl, Br, $CF_3$, $OCH_2CH_2OCH_3$, $C_1$-$C_3$ alkyl, $C_1$-$C_3$ haloalkyl, $C_1$-$C_3$ alkoxy, or $C_1$-$C_3$ alkylthio;

X is $OR^6$; and $R^6$ is H, $C_1$-$C_3$ alkyl or $C(O)CH_3$.

4. The compounds of claim 1 where $R_2$ is

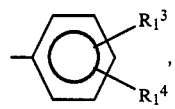

$R_3$, $R_4$, $R_1^3$ and $R_1^4$ are independently H, F, Cl, Br, $CF_3$, CN, $OCH_2CH_2OCH_3$, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio each substituted at the 3, 4 or 5 position.

5. The compounds of claim 4 where $R^3$, $R^4$, $R_1^3$ and $R_1^4$ are independently H, F, Cl, $CF_3$, $C_1$-$C_3$ alkoxy, or $C_1$-$C_3$ alkyl and X is OH or $OCH_3$.

6. The compound of claim 5 which is α,α-bis(4-chlorophenyl)-2-oxiranemethanol.

7. The compound of claim 5 which is α-phenyl-α-oxiranemethanol.

8. The compound of claim 5 which is α,α-bis(4-fluorophenyl)-2-oxiranemethanol.

9. The compound of claim 5 which is α-(4-chlorophenyl)-α-phenyloxiranemethanol.

10. The compound of claim 5 which is α-(4-chlorophenyl)-α-(3,5-dichlorophenyl)oxiranemethanol.

11. An agriculturally suitable composition for controlling the growth of undesired vegetation comprising an effective amount of the compound of claim 1 and at least one of the following: surfactant, solid or liquid diluent.

12. An agriculturally suitable composition for controlling the growth of undesired vegetation comprising an effective amount of the compound of claim 2 and at least one of the following: surfactant, solid or liquid diluent.

13. An agriculturally suitable composition for controlling the growth of undesired vegetation comprising an effective amount of the compound of claim 3 and at least one of the following: surfactant, solid or liquid diluent.

14. An agriculturally suitable composition for controlling the growth of undesired vegetation comprising an effective amount of the compound of claim 4 and at least one of the following: surfactant, solid or liquid diluent.

15. An agriculturally suitable composition for controlling the growth of undesired growth of undesired vegetation comprising an effective amount of the compound of claim 5 and at least one of the following: surfactant, solid or liquid diluent.

16. An agriculturally suitable composition for controlling the growth of undesired vegetation comprising an effective amount of the compound of claim 6 and at least one of the following: surfactant, solid or liquid diluent.

17. An agriculturally suitable composition for controlling the growth of undesired vegetation comprising an effective amount of the compound of claim 7 and at least one of the following: surfactant, solid or liquid diluent.

18. An agriculturally suitable composition for controlling the growth of undesired vegetation comprising an effective amount of the compound of claim 8 and at least one of the following: surfactant, solid or liquid diluent.

19. An agriculturally suitable composition for controlling the growth of undesired vegetation comprising an effective amount of the compound of claim 9, and at least one of the following: surfactant, solid or liquid diluent.

20. An agriculturally suitable composition for controlling the growth of undesired vegetation comprising an effective amount of the compound of claim 10 and at least one of the following: surfactant, solid or liquid diluent.

21. A method for controlling the growth of undesired vegetation in crops which comprises applying to the locus of the crop to be protected an effective amount of a compound of claim 1.

22. A method for controlling the growth of undesired vegetation in crops which comprises applying to the locus of the crop to be protected an effective amount of a compound of claim 2.

23. A method for controlling the growth of undesired vegetation in crops which comprises applying to the locus of the crop to be protected an effective amount of a compound of claim 3.

24. A method for controlling the growth of undesired vegetation in crops which comprises applying to the locus of the crop to be protected an effective amount of a compound of claim 4.

25. A method for controlling the growth of undesired vegetation in crops which comprises applying to the locus of the crop to be protected an effective amount of a compound of claim 5.

26. A method for controlling the growth of undesired vegetation in crops which comprises applying to the locus of the crop to be protected an effective amount of a compound of claim 6.

27. A method for controlling the growth of undesired vegetation in crops which comprises applying to the locus of the crop to be protected an effective amount of a compound of claim 7.

28. A method for controlling the growth of undesired vegetation in crops which comprises applying to the locus of the crop to be protected an effective amount of a compound of claim 8.

29. A method for controlling the growth of undesired vegetation in crops which comprises applying to the locus of the crop to be protected an effective amount of a compound of claim 9.

30. A method for controlling the growth of undesired vegetation in crops which comprises applying to the locus of the crop to be protected an effective amount of a compound of claim 10.

31. A method for controlling the growth of undesired vegetation in rice which comprises applying to the locus to be protected an effective amount of a compound of claim 1 of the formula I.

32. A method for controlling the growth of undesired vegetation in rice which comprises applying to the locus to be protected an effective amount of a compound of claim 5 of Formula I.

33. A method for controlling the growth of undesired vegetation in rice which comprises applying to the locus to be protected an effective amount of the compound of claim 6.

34. A method for controlling the growth of undesired vegetation in rice which comprises applying to the locus to be protected an effective amount of the compound of claim 7.

35. A method for controlling the growth of undesired vegetation in rice which comprises applying to the locus to be protected an effective amount of the compound of claim 7.

36. A method for controlling the growth of undesired vegetation in rice which comprises applying to the locus to be protected an effective amount of the compound of claim 10.

* * * * *